(12) United States Patent
Svendsen et al.

(10) Patent No.: US 8,008,057 B2
(45) Date of Patent: Aug. 30, 2011

(54) SUBTILASES

(75) Inventors: Allan Svendsen, Horsholm (DK); Stefan Minning, Frederiksberg C (DK)

(73) Assignee: Novozymes A/S, Bagsvaerd (DK)

( * ) Notice: Subject to any disclaimer, the term of this patent is extended or adjusted under 35 U.S.C. 154(b) by 113 days.

(21) Appl. No.: 12/401,077

(22) Filed: Mar. 10, 2009

(65) Prior Publication Data

US 2009/0203111 A1    Aug. 13, 2009

Related U.S. Application Data

(62) Division of application No. 10/807,096, filed on Mar. 22, 2004, now Pat. No. 7,727,756.

(60) Provisional application No. 60/457,798, filed on Mar. 26, 2003.

(30) Foreign Application Priority Data

Mar. 21, 2003    (DK) .................... 2003 00435

(51) Int. Cl.
*C12N 9/54* (2006.01)
*C11D 3/386* (2006.01)
*C12N 15/57* (2006.01)
*C12N 15/74* (2006.01)
*C12N 15/75* (2006.01)

(52) U.S. Cl. .............. 435/221; 435/69.1; 435/252.3; 435/252.31; 435/320.1; 536/23.2; 510/300

(58) Field of Classification Search .............. None
See application file for complete search history.

(56) References Cited

U.S. PATENT DOCUMENTS

| | | | |
|---|---|---|---|
| 5,397,705 A | 3/1995 | Zukowski et al. |
| 5,798,234 A | 8/1998 | Engel et al. |
| 5,891,701 A | 4/1999 | Sloma et al. |
| 6,376,227 B1 | 4/2002 | Takaiwa et al. |
| 6,803,222 B2 | 10/2004 | Hatada et al. |
| 7,294,499 B2 | 11/2007 | Svendsen et al. |

FOREIGN PATENT DOCUMENTS

| | | |
|---|---|---|
| EP | 204 342 | 2/1992 |
| EP | 1209233 | 5/2002 |
| JP | 4197182 | 7/1992 |
| WO | WO 88/01293 | 2/1988 |
| WO | WO 92/17577 | 10/1992 |
| WO | WO 96/09396 | 3/1996 |
| WO | WO 98/56927 | 12/1998 |
| WO | WO 00/26230 | 5/2000 |
| WO | WO 01/66712 | 9/2001 |
| WO | WO 2004/067737 | 8/2004 |

OTHER PUBLICATIONS

Almog et al, "The 0.93 A° Crystal Structure of Sphericase: A Calcium-loaded Serine Protease from *Bacillus sphaericus*," Journal of Molecular Biology, vol. 332, pp. 1071-1082 (2003).

Davail et al, "Cold Adaptation of Proteins," The Journal of Biological Chemistry, vol. 269, No. 26, pp. 17448-17453 (1994).

(Continued)

*Primary Examiner* — Karen Carlson
*Assistant Examiner* — William W Moore
(74) *Attorney, Agent, or Firm* — Kristin J. McNamara

(57) ABSTRACT

The present invention relates to methods for producing variants of a parent JP170 subtilase and of a parent BPN' subtilase and to JP170 and BPN' variants having altered properties as compared to the parent JP170/BPN' subtilase.

15 Claims, 4 Drawing Sheets

OTHER PUBLICATIONS

Derwent record for JP 7-62152/JP95062152-B2, "Detergent Compsn. Contg. Alkali Protease—Produced by *Bacillus* Species Y and an Alkali Builder with Specified Acid Dissociation Constant Range," Lion Corp. Derwent Primary Accession No. 1988-164153 (Jul. 5, 1995).

Graycar et al, "Engineered *Bacillus lentus* Subtilisins Having Altered Flexibility," Journal of Molecular Biology, vol. 292, pp. 97-109 (1999).

Gupta et al, "Bacterial Alkaline Proteases: Molecular Approaches and Industrial Applications," Applied Microbial Biotechnology, vol. 59, pp. 15-32 (2002).

Mei et al, "Engineering Subtilisin YaB: Restriction of Substrate Specificity by the Substitution of Gly124 and Gly151 with Ala," Protein Engineering, vol. 11, No. 2, pp. 109-117 (1998).

Narinx et al, "Subtilisin from Psychrophilic Antarctic Bacteria: Characterization and Site-directed Mutagenesis of Residues Possibly Involved in the Adaptation to Cold," Protein Engineering, vol. 10, No. 11, pp. 1271-1279 (1997).

Saeki et al, "Novel Oxidatively Stable Subtilisin-like Serine Proteases from Alkaliphilic *Bacillus* spp.: Enzymatic Properties, Sequences, and Evolutionary Relationships," Biochemical and Biophysical Research Communications, vol. 279, pp. 313-319 (2000).

Siezen, "Homology Modelling of the Catalytic Domain of Human Furin: A Model for the Eukaryotic Subtilisin-like Proprotein Convertases," European Journal of Biochemistry, vol. 222, pp. 255-266 (1994).

Siezen, "Modelling and Engineering of Enzyme/Substrate Interactions in Subtilisin-like Enzymes of Unknown 3-Dimensional Structure," in Subtilisin Enzymes: Practical Protein Engineering, R. Bott and C. Betzel., Ed., Plenum Press New York, pp. 63-73 (1996).

Siezen et al, "Subtilases: The Superfamily of Subtilisin-like Serine Proteases," Protein Science, vol. 6, pp. 501-523 (1997).

Strausberg et al, Biotechnology vol. 13, No. (7), pp. 669-673 (1995).

Wintrode et al, Journal Biology and Chemistry, vol. 275, No. 41, pp. 31635-31640 (2000).

Miyazaki et al, JMB, J. Mol. Biol., vol. 297, pp. 1015-1026 (2000).

Gallagher et al, Prot Struc Funct Genet. vol. 10, No. 2, pp. 205-213 (1993).

```
         1                                                              60
a)   NDVARGIVKA DVAQNNYGLY GQGQVVAVAD TGLDTGRNDS SMHEAFRGKI TALYALGRTN
b)   NDVARGIVKA DVAQNNYGLY GQGQLVAVAD TGLDTGRNDS SMHEAFRGKI TALYALGRTN
c)   NDVARGIVKA DVAQNNFGLY GQGQIVAVAD TGLDTGRNDS SMHEAFRGKI TALYALGRTN 61                                                             120
a)   NANDPNGHGT HVAGSVLGNA LNKGMAPQAN LVFQSIMDSS GGLGGLPSNL NTLFSQAWNA
b)   NASDPNGHGT HVAGSVLGNA LNKGMAPQAN LVFQSIMDSS GGLGGLPSNL NTLFSQAWNA
c)   NANDPNGHGT HVAGSVLGNA TNKGMAPQAN LVFQSIMDSG GGLGGLPANL QTLFSQAYSA 121                                                            180
a)   GARIHTNSWG APVNGAYTAN SRQVDEYVRN NDMTVLFAAG NEGPNSGTIS APGTAKNAIT
b)   GARIHTNSWG APVNGAYTAN SRQVDEYVRN NDMTVLFAAG NEGPNSGTIS APGTAKNAIT
c)   GARIHTNSWG APVNGAYTTD SRNVDDYVRK NDMTILFAAG NEGPGSGTIS APGTAKNAIT 181                                                            240
a)   VGATENYRPS FGSLADNPNH IAQFSSRGAT RDGRIKPDVT APGTFILSAR SSLAPDSSFW
b)   VGATENYRPS FGSIADNPNH IAQFSSRGAT RDGRIKPDVT APGTFILSAR SSLAPDSSFW
c)   VGATENLRPS FGSYADNINH VAQFSSRGPT RDGRIKPDVM APGTYILSAR SSLAPDSSFW 241                                                            300
a)   ANYNSKYAYM GGTSMATPIV AGNVAQLREH FIKNRGITPK PSLIKAALIA GATDVGLGYP
b)   ANYNSKYAYM GGTSMATPIV AGNVAQLREH FIKNRGITPK PSLIKAALIA GATDVGLGYP
c)   ANHDSKYAYM GGTSMATPIV AGNVAQLREH FVKNRGVTPK PSLLKAALIA GAADVGLGFP 301                                                            360
a)   SGDQGWGRVT LDKSLNVAYV NEATALATGQ KATYSFQAQA GKPLKISLVW TDAPGSTTAS
b)   SGDQGWGRVT LDKSLNVAYV NEATALATGQ KATYSFQAQA GKPLKISLVW TDAPGSTTAS
c)   NGNQGWGRVT LDKSLNVAFV NETSPLSTSQ KATYSFTAQA GKPLKISLVW SDAPGSTTAS 361                                                            420
a)   YTLVNDLDLV ITAPNGQKYV GNDFSYPYDN NWDGRNNVEN VFINAPQSGT YTIEVQAYNV
b)   YTLVNDLDLV ITAPNGQKYV GNDFSYPYDN NWDGRNNVEN VFINAPQSGT YIIEVQAYNV
c)   LTLVNDLDLV ITAPNGTKYV GNDFTAPYDN NWDGRNNVEN VFINAPQSGT YTVEVQAYNV 421        433
a)   PSGPQRFSLA IVH
b)   PSGPQRFSLA IVH
c)   PVSPQTFSLA IVH
```

Fig. 1

|    | 1   | 2   | 3   | 4   | 5   | 6   | 7   | 8   | 9   | 10  | 11  | 12  | 13  | 14  | 15  | 16  | 17  |
|----|-----|-----|-----|-----|-----|-----|-----|-----|-----|-----|-----|-----|-----|-----|-----|-----|-----|
| 1  | 100 | 94  | 53  | 53  | 51  | 53  | 53  | 52  | 52  | 53  | 55  | 52  | 52  | 51  | 51  | 51  | 50  |
| 2  |     | 100 | 52  | 53  | 53  | 51  | 51  | 49  | 50  | 51  | 50  | 54  | 54  | 53  | 54  | 54  | 54  |
| 3  |     |     | 100 | 93  | 76  | 51  | 50  | 51  | 55  | 52  | 54  | 58  | 58  | 59  | 57  | 60  | 60  |
| 4  |     |     |     | 100 | 75  | 52  | 52  | 52  | 56  | 51  | 55  | 58  | 58  | 61  | 58  | 62  | 61  |
| 5  |     |     |     |     | 100 | 60  | 60  | 60  | 58  | 60  | 62  | 58  | 57  | 59  | 59  | 62  | 59  |
| 6  |     |     |     |     |     | 100 | 99  | 99  | 97  | 91  | 46  | 63  | 69  | 74  | 66  | 74  | 74  |
| 7  |     |     |     |     |     |     | 100 | 99  | 97  | 90  | 76  | 69  | 74  | 66  | 74  | 74  | 56  |
| 8  |     |     |     |     |     |     |     | 100 | 98  | 91  | 77  | 63  | 69  | 74  | 66  | 74  | 74  |
| 9  |     |     |     |     |     |     |     |     | 100 | 88  | 79  | 69  | 67  | 74  | 74  | 74  | 74  |
| 10 |     |     |     |     |     |     |     |     |     | 100 | 77  | 66  | 71  | 74  | 67  | 74  | 74  |
| 11 |     |     |     |     |     |     |     |     |     |     | 100 | 64  | 69  | 74  | 67  | 73  | 73  |
| 12 |     |     |     |     |     |     |     |     |     |     |     | 100 | 99  | 76  | 72  | 76  | 76  |
| 13 |     |     |     |     |     |     |     |     |     |     |     |     | 100 | 76  | 76  | 76  | 76  |
| 14 |     |     |     |     |     |     |     |     |     |     |     |     |     | 100 | 99  | 99  | 99  |
| 15 |     |     |     |     |     |     |     |     |     |     |     |     |     |     | 100 | 99  | 99  |
| 16 |     |     |     |     |     |     |     |     |     |     |     |     |     |     |     | 100 | 98  |
| 17 |     |     |     |     |     |     |     |     |     |     |     |     |     |     |     |     | 100 |

Fig. 3

```
1)    AVPS-TQTPW  GIKSIYNDQS  ITK-TTGGSG  IKVAVLDTGV  YT------SH  LDLAGSAEQC
2)    ----AQSVPY  GVSQIKAPAL  HSQ-GYTGSN  VKVAVIDSGI  DS------SH  PDLK--VAGG
3)    ----AQSVPW  GISRVQAPAA  HNR-GLTGSG  VKVAVLDTGI  S-------TH  PDL--NIRGG
4)    -------NDV  ARGIVKADVA  QNNFGLYGQG  QIVAVADTGL  DTGRNDSSMH  EAFRGKITAL
      1                                                                  53

1)    KDFTQSNPLV  DGSC-TDRQG  HGTHVAGTVL  AHGGSNGQGV  YGVAPQAKLW  AYKVLGD-NG
2)    ASMVPSET--  --PNFQDDNS  HGTHVAGTVA  ALN--NSIGV  LGVAPSSALY  AVKVLGD AG
3)    ASFVPGEP--  --ST-QDGNG  HGTHVAGTIA  ALN--NSIGV  LGVAPSAELY  AVKVLGA-SG
4)    YALG-RTN--  --NA-NDPNG  HGTHVAGSVL  GN---ATNKG  MAPQANLVFQ  SIMD-SGGGL
      54                                                                106

1)    SGY--SDD-I  AAAIRHVADE  ASRTGSKVVI  NMSLGSSA--  -KDSLIASAV  DYAY-GKGVL
2)    SGQ--YSW-I  INGIEWAIAN  N-----MDVI  NMSLGGPS--  -GSAALKAAV  DKAV-ASGVV
3)    SGS--VSS-I  AQGLEWAGNN  G-----MHVA  NLSLGSPS--  -PSATLEQAV  NSAT-SRGVL
4)    GGLPA-NLQT  LFSQAYSAGA  R-----IHTN  SWGAPVNGAY  TTDSRN-VDD  YVRKNDMTIL
      107                                                               156

1)    IVAAAGNSGS  G---SNTIGF  PGGLVNAVAV  AALEN-----  -----VQQNG  TYRVADFSSR
2)    VVAAAGNEG-  STGSSSTVGY  PGKYPSVIAV  GAVDS-----  -----S----  -NQRASFSSV
3)    VVAASGNSGA  -----GSISY  PARYANAMAV  GATDQ-----  -----N----  -NNRASFSQY
4)    FAAGNEGPGS  G---TISAPG  TAKNAITVGA  TENLRPSFGS  YADNIN----  -HVAQFSSRG
      157                                                               208

1)    GNPATAGDYI  IQERDIEVSA  PGASVESTWY  T---------  ---GGYNTIS  GTSMATPHVA
2)    GP--------  ----ELDVMA  PGVSIQSTLP  G---------  ---NKYGAYN  GTSMASPHVA
3)    GA--------  ----GLDIVA  PGVNVQSTYP  G---------  ---STYASLN  GTSMATPHVA
4)    PTRDGRIK--  ----PDVMAP  GTYILSARSS  LAPDSSFWAN  HDSKYAYMGG  TSMATPIVAG
      209                                                               262

1)    GLAAKIWSAN  T-----SLSH  SQLRTELQNR  AKVYDIKGGI  GAGTGDDYAS  GFGYPRVK--
2)    GAAALILSKH  P-----NWTN  TQVRSSLQNT  T--TKLG---  -----DSFYY  GKGLINVQAA
3)    GAAALVKQKN  P-----SWSN  VQIRNHLKNT  A--TSLG---  -----STNLY  GSGLVNAEAA
4)    NVAQLREHFV  KNRGVTPKPS  LLKAALIAGA  A--DVGLGFP  -----NGNQG  WGRVTLDKSL
      263                                                               315

1)    ----------  ----------  ----------  ----------  ----------  ----------
2)    AQ--------  ----------  ----------  ----------  ----------  ----------
3)    TR--------  ----------  ----------  ----------  ----------  ----------
4)    NVAFVNETSP  LSTSQKATYS  FTAQAGKPLK  ISLVWSDAPG  STTASLTLVN  DLDLVITAPN
      316                                                               375

1)    ----------  ----------  ----------  ----------  ----------  --------
2)    ----------  ----------  ----------  ----------  ----------  --------
3)    ----------  ----------  ----------  ----------  ----------  --------
4)    GTKYVGNDFT  APYDNNWDGR  NNVENVFINA  PQSGTYTVEV  QAYNVPVGPQ  TFSLAIVH
      376                                                               433
```

SUBTILASES

CROSS-REFERENCE TO RELATED APPLICATIONS

This application is a divisional of application Ser. No. 10/807,096 filed on Mar. 22, 2004 (now U.S. Pat. No. 7,727,756) which claims priority or the benefit under 35 U.S.C. 119 of Danish application no. PA 2003 00435 filed Mar. 21, 2003 and U.S. provisional application No. 60/457,798 filed Mar. 26, 2003, the contents of which are fully incorporated herein by reference.

FIELD OF THE INVENTION

The present invention relates to JP170 and BPN' like subtilases and to methods of construction such variants with altered properties, such as stability (e.g. thermostability or storage stability), $Ca^{2+}$ dependency, pH dependent activity, improved performance in washing and cleaning applications.

BACKGROUND OF THE INVENTION

Enzymes have been used within the detergent industry as part of washing formulations for more than 30 years. Proteases are from a commercial perspective the most relevant enzyme in such formulations, but other enzymes including lipases, amylases, cellulases or mixtures of enzymes are also often used.

To improve the cost and/or the performance of proteases there is an ongoing search for proteases with altered properties, such as increased activity at low temperatures, increased thermostability, increased specific activity at a given pH, altered $Ca^{2+}$ dependency, increased stability in the presence of other detergent ingredients (e.g. bleach, surfactants etc.) etc.

The search for proteases with altered properties include both discovery of naturally occurring proteases, i.e. so called wild-type proteases but also alteration of well-known proteases by e.g. genetic manipulation of the nucleic acid sequence encoding said proteases. Knowledge of the relationship between the three-dimensional structure and the function of a protein has improved the ability to evaluate which areas of a protein to alter to affect a specific characteristic of the protein.

One family of proteases, which are often used in detergents, are the subtilases. This family has previously been further grouped into 6 different sub-groups by Siezen R J and Leunissen J A M, 1997, Protein Science, 6, 501-523. One of these sub-groups is the Subtilisin family which includes subtilases such as BPN', subtilisin 309 (SAVINASE®, NOVOZYMES A/S), subtilisin Carlsberg (ALCALASE®, NOVOZYMES A/S), subtilisin S41 (a subtilase from the psychrophilic Antarctic *Bacillus* TA41, Davail S et al. 1994, The Journal of Biological Chemistry, 269(26), 99. 17448-17453), subtilisin S39 (a subtilase from the psychrophilic Antarctic *Bacillus* TA39, Narinx E et al. 1997, Protein Engineering, 10 (11), pp. 1271-1279) and TY145 (a subtilase from *Bacillus* sp. TY145, NCIMB 40339 described in WO 92/17577).

The groupings indicated above were made based on primary sequence alignments, with only little consideration of three-dimensional structure. However, despite sequence homologies between subtilases belonging to the Subtilisin subgroup, modelling of the three-dimensional structure of one subtilase on the basis of the three-dimensional structure of another subtilase (such as the subtilisin BPN' that was used by Siezen and Leunissen) may result in an incorrect three-dimensional model structure because of structural differences.

Recently the three-dimensional structure of subtilase TY145 have been elucidated and it was found that there are several differences between this and the three-dimensional structure of BPN' also belonging to the Subtilisin subgroup of subtilases (PCT/DK2004/000066).

The differences between the three-dimensional structures of TY145 and BPN' are confirmed by the three-dimensional structure of the subtilase "sphericase" from *Bacillus sphaericus* (PDB NO:1EA7, Protein Data Bank). The overall structure and many details of this subtilase are very homologous with the TY145 subtilase structure.

The subtilase JP170 and subtilases similar to JP170 are already known in the art, but the three-dimensional structure has not been disclosed for such subtilases.

The JP170 subtilase was described as protease A in WO 88/01293 to Novozymes. Later the patent application WO 98/56927 to Novozymes Biotech disclosed the amino acid (polypeptide) sequence of JP170 and the DNA sequence encoding JP170. In EP 204 342 the protease Ya was disclosed, and JP7-62152 and JP 4197182 to Lion Corp. disclosed the DNA sequence encoding protease Ya produced by *Bacillus* sp. Y that is homologous to JP170. In addition U.S. Pat. No. 6,376,227 to Kao Corp. discloses physical characteristics as well as DNA and polypeptide sequences of alkaline proteases KP43, KP1790 and KP9860 which are also homologous to JP170. Recently variants of the KP43, KP9860, SD-521 and Ya proteases among others were disclosed in EP 1209233. These proteases are highly homologous, and an alignment of KP43, KP9860, SD-521, Y and JP170 revealed at least 90% homology. Therefore JP170, Ya and SD-521 represent these proteases in the alignment of FIG. 1 of the present specification.

BRIEF DESCRIPTION OF THE FIGURES

FIG. 1 shows an alignment of three JP170 type proteases: (a) SD-521 (SEQ ID NO: 3) (EP 1 209 233), (b) protease Ya (SEQ ID NO: 2) (WO 99/67370), and (c) JP170 (SEQ ID NO: 1) (WO 98/56927, mature sequence from Appendix 1).

FIG. 3 shows a matrix of homology between amino acid sequences of subtilases pertaining to various subtilase subgroups. The sequences are identified by sequence database accession numbers and their derivation.

Figure 2:
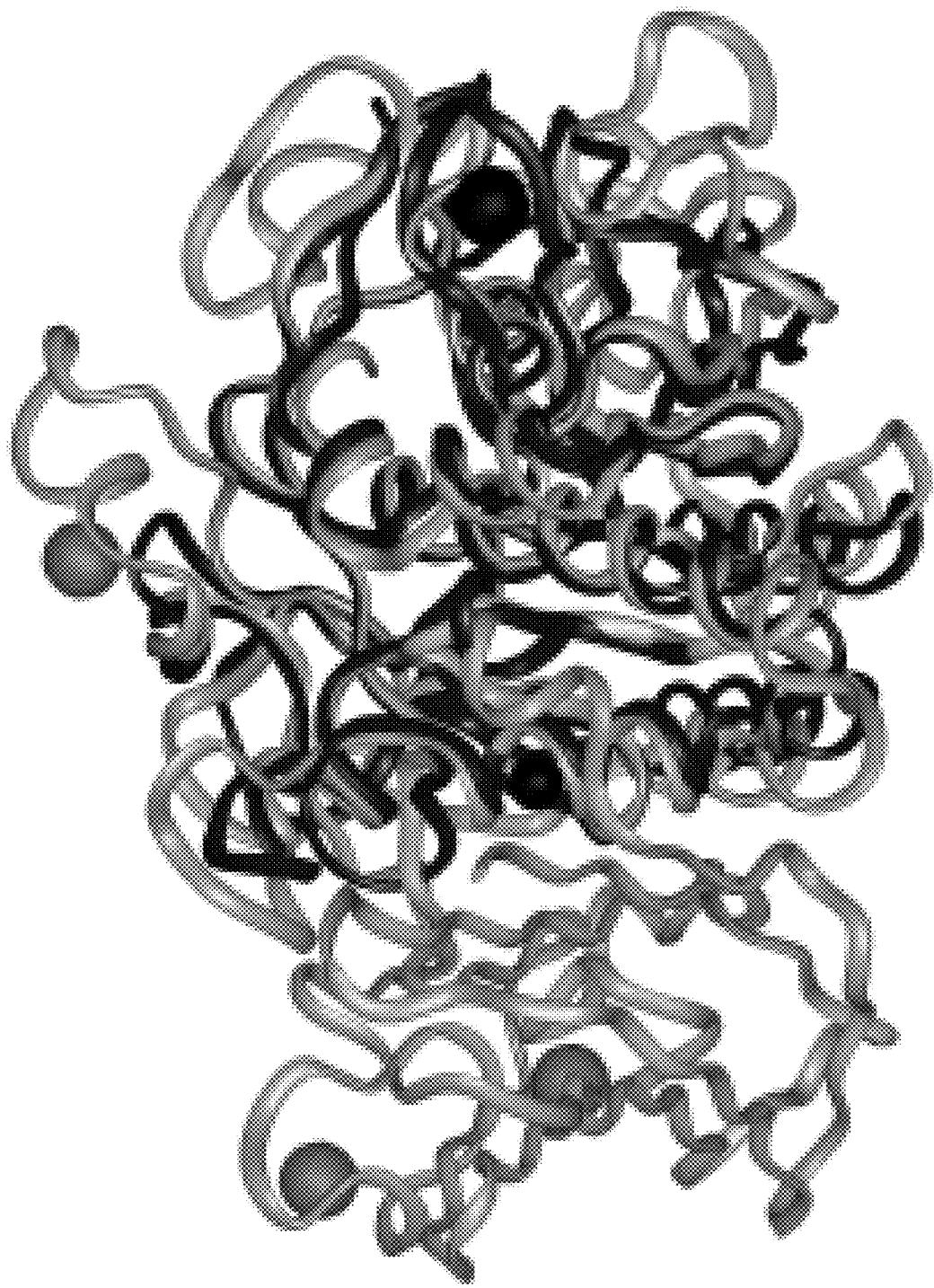
FIG. 2 shows a superposition of the 3D structures of the proteases JP170 (SEQ ID NO:1) and Savinase (SEQ ID NO:8) (BLSAVI), with indication of calcium binding sites. In the figure JP170 (SEQ ID NO:1) is indicated in light grey with three ion-binding sites, and Savinase (SEQ ID NO: 8) in a dark structure with two ion-binding sites.

1: aam50084; Subtilase derived from *Bacillus* sp. strain SD-521
2: aaw89547; Subtilase derived from *Bacillus* sp. JP170
3: q45681; Subtilase derived from *B. subtilis* (BSTA41)
4: p28842; Psychrophilic subtilisin derived from Antarctic *Bacillus* strain (BSTA39)
5: abb77095; Subtilase derived from *Bacillus* sp. (TY145)
6: p00783; Subtilase derived from *Bacillus subtilis* var. *amylosacchariticus* (BSAMY)
7: p29142; Subtilase derived from *Bacillus stearothermophilus* (BSSJ)
8: p35835; Subtilase derived from *Bacillus subtilis* var. *natto*. (BSNAT)
9: p07518; Subtilase derived from *Bacillus pumilus* (*B. mesentericus*) (BPMES)

10: p00782; Subtilase derived from *Bacillus amyloliquefaciens* (BPN')
11: p00780; Subtilase derived from *Bacillus licheniformis* (BLSCAR)
12: p41363; Subtilase derived from *Bacillus halodurans* (BHSAH)
13: aaw62222; Subtilase derived from *Bacillus lentus* (BLS147)
14: p29600; Subtilase derived from *Bacillus lentus* (BLSAVI, BLS309)
15: p27693; Subtilase derived from *Bacillus alcalophilus* (BAALKP)
16: q99405; Subtilase derived from *Bacillus* sp. strain KSM-K16 (BSKSMK)
17: p29599; Subtilase derived from *Bacillus lentus* (BLSUBL).

Sequences 1 and 2 belong to the JP170 type, sequences 3 to 5 belong to the TY145 type, sequences 6 to 11 belong to the "true subtilisins" or I-S1 type, and sequences 12 to 17 belong to the "highly alkaline" subtilisins or I-S2 type. From FIG. 3 it is clear that these types are quite distinct.

FIG. 4 shows a three-dimensional alignment of the subtilases: (1) Ty145 (SEQ ID NO: 7); (2) BPN' (SEQ ID NO: 4); (3) Savinase (SEQ ID NO:8); and (4) JP170 (SEQ ID NO: 1).

By 3D sequences is meant that the position of homologous residues are chosen by superposition of the 3D structures and subsequently the amino acid sequences are aligned based on these homologous positions.

BRIEF DESCRIPTION OF THE APPENDIX

APPENDIX 1 shows the structural coordinates for the solved crystal structure of JP170 (SEQ ID NO: 1).
Sequence Listing
In the appended sequence listing the following amino acid sequences are provided:
Subtilase JP170 (SEQ ID NO:1)
Subtilase Y (SEQ ID NO:2)
Subtilase SD-521 (SEQ ID NO:3)
Subtilase BPN' (SEQ ID NO:4)
Partiel sequence (SEQ ID NO:5)
Partiel sequence (SEQ ID NO:6)
Subtilase TY145 (SEQ ID NO:7)
SAVINASE® (SEQ ID NO:8)

BRIEF DESCRIPTION OF THE INVENTION

Now the inventors of the present invention disclose the three-dimensional structure of the subtilase JP170 (SEQ ID NO: 1). This subtilase has large structural differences to the structures of the subtilisins BPN' (SEQ ID NO: 4) and TY145 (SEQ ID NO:7).

Based on these differences the inventors have modified the amino acid sequence of subtilases having a JP170 type structure and subtilases having a BPN' type structure to obtain variants with improved properties. The variants have altered properties, such as increased activity at low temperatures, increased thermostability, increased specific activity at a given pH, altered $Ca^{2+}$ dependency, increased stability in the presence of other detergent ingredients (e.g. bleach, surfactants etc.) etc.

Accordingly, the object of the present invention is to provide a method for constructing subtilases having altered properties, in particular to provide a method for constructing subtilases having altered properties as described above.

Thus the present invention relates to a method for constructing a variant of a parent subtilase, wherein the variant has at least one altered property as compared to said parent subtilase, which method comprises:
  a) analyzing the three-dimensional structure of the subtilase to identify, on the basis of an evaluation of structural considerations in relation to a JP170 three dimensional structure, at least one amino acid residue or at least one structural region of the subtilase, which is of relevance for altering said property;
  b) modifying the DNA of the polynucleotide encoding the parent to construct a polynucleotide encoding a variant subtilase, which in comparison to the parent subtilase, has been modified by deletion, substitution or insertion of the amino acid residue or structural part identified in i) so as to alter said property;
  c) expressing the variant subtilase in a suitable host, and
  d) testing the resulting subtilase variant for said property.

More specifically the invention relates to a method of producing a subtilase variant, wherein the variant has at least one altered property as compared to a parent subtilase, which method comprises:
  a) producing a model structure of the parent subtilase on the three-dimensional structure of BPN' (SEQ ID NO: 4), TY145 (SEQ ID NO: 7) or JP170 (SEQ ID NO: 1); or producing an actually determined three-dimensional structure of the parent subtilase,
  b) comparing the model or actual three-dimensional structure of the parent subtilase to the JP170 (SEQ ID NO:1) structure by superimposing the structures through matching the CA, CB, C, O, and N atoms of the active site residues,
  c) identifying on the basis of the comparison in step b) at least one structural part of the parent subtilase, wherein an alteration in said structural part is predicted to result in an altered property;
  d) modifying the nucleic acid sequence encoding the parent subtilase to produce a nucleic acid sequence encoding at least one deletion or substitution of one or more amino acids at a position corresponding to said structural part, or at least one insertion of one or more amino acid residues in positions corresponding to said structural part;
  e) performing steps c) and d) iteratively N times, where N is an integer with the value of one or more;
  f) preparing the variant resulting from steps a)-e);
  g) testing the properties of said variant; and
  h) optionally repeating steps a)-g) recursively; and
  i) selecting a subtilase variant having at least one altered property as compared to the parent subtilase.
  j) expressing the modified nucleic acid sequence in a host cell to produce the variant subtilase;
  k) isolating the produced subtilase variant;
  l) purifying the isolated subtilase variant and
  m) recovering the purified subtilase variant.

Although it has been described in the following that modification of the parent subtilase in certain regions and/or positions is expected to confer a particular effect to the thus produced subtilase variant, it should be noted that modification of the parent subtilase in any of such regions may also give rise to any other of the above-mentioned effects. For example, any of the regions and/or positions mentioned as being of particular interest with respect to, e.g., improved thermostability, may also give rise to, e.g., higher activity at a lower pH, an altered pH optimum, or increased specific activity, such as increased peptidase activity.

Further aspects of the present invention relates to variants of a subtilase, the DNA encoding such variants and methods of preparing the variants. Still further aspects of the present invention relates to the use of the variants for various industrial purposes, in particular as an additive in detergent compositions. Other aspects of the present invention will be apparent from the below description as well as from the appended claims.

DEFINITIONS

Prior to discussing this invention in further detail, the following terms and conventions will first be defined.

For a detailed description of the nomenclature of amino acids and nucleic acids, we refer to WO 00/71691 page 5, hereby incorporated by reference. A description of the nomenclature of modifications introduced in a polypeptide by genetic manipulation can be found in WO 00/71691 page 7-12, hereby incorporated by reference.

The term "subtilases" refer to a sub-group of serine protease according to Siezen et al., *Protein Engng.* 4 (1991) 719-737 and Siezen et al. *Protein Science* 6 (1997) 501-523. Serine proteases or serine peptidases is a subgroup of proteases characterised by having a serine in the active site, which forms a covalent adduct with the substrate. Further the subtilases (and the serine proteases) are characterised by having two active site amino acid residues apart from the serine, namely a histidine and an aspartic acid residue.

Subtilases are defined by homology analysis of more than 170 amino acid sequences of serine proteases previously referred to as subtilisin-like proteases. The subtilases may be divided into 6 sub-divisions, i.e. the Subtilisin family, the Thermitase family, the Proteinase K family, the Lantibiotic peptidase family, the Kexin family and the Pyrolysin family.

The Subtilisin family (EC 3.4.21.62) may be further divided into 3 sub-groups, i.e. I-S1 ("true" subtilisins), I-S2 (highly alkaline proteases) and intracellular subtilisins. Definitions or grouping of enzymes may vary or change, however, in the context of the present invention the above division of subtilases into sub-division or sub-groups shall be understood as those described by Siezen et al., *Protein Engng.* 4 (1991) 719-737 and Siezen et al. *Protein Science* 6 (1997) 501-523.

The term "parent" is in the context of the present invention to be understood as a protein, which is modified to create a protein variant. The parent protein may be a naturally occurring (wild-type) polypeptide or it may be a variant thereof prepared by any suitable means. For instance, the parent protein may be a variant of a naturally occurring protein which has been modified by substitution, chemical modification, deletion or truncation of one or more amino acid residues, or by addition or insertion of one or more amino acid residues to the amino acid sequence, of a naturally-occurring polypeptide. Thus the term "parent subtilase" refers to a subtilase which is modified to create a subtilase variant.

The term "variant" is in the context of the present invention to be understood as a protein which has been modified as compared to a parent protein at one or more amino acid residues.

The term "modification(s)" or "modified" is in the context of the present invention to be understood as to include chemical modification of a protein as well as genetic manipulation of the DNA encoding a protein. The modification(s) may be replacement(s) of the amino acid side chain(s), substitution (s), deletion(s) and/or insertions in or at the amino acid(s) of interest. Thus the term "modified protein", e.g. "modified subtilase", is to be understood as a protein which contains modification(s) compared to a parent protein, e.g. subtilase.

"Homology" or "homologous to" is in the context of the present invention to be understood in its conventional meaning and the "homology" between two amino acid sequences should be determined by use of the "Similarity" defined by the GAP program from the University of Wisconsin Genetics Computer Group (UWGCG) package using default settings for alignment parameters, comparison matrix, gap and gap extension penalties. Default values for GAP penalties, i.e. GAP creation penalty of 3.0 and GAP extension penalty of 0.1 (Program Manual for the Wisconsin Package, Version 8, August 1994, Genetics Computer Group, 575 Science Drive, Madison, Wis., USA 53711). The method is also described in S. B. Needleman and C. D. Wunsch, Journal of Molecular Biology, 48, 443-445 (1970). Identities can be extracted from the same calculation. The homology between two amino acid sequences can also be determined by "identity" or "similarity" using the GAP routine of the UWGCG package version 9.1 with default setting for alignment parameters, comparison matrix, gap and gap extension penalties can also be applied using the following parameters: gap creation penalty=8 and gap extension penalty =8 and all other parameters kept at their default values. The output from the routine is besides the amino acid alignment the calculation of the "Percent Identity" and the "Similarity" between the two sequences. The numbers calculated using UWGCG package version 9.1 is slightly different from the version 8.

The term "position" is in the context of the present invention to be understood as the number of an amino acid in a peptide or polypeptide when counting from the N-terminal end of said peptide/polypeptide. The position numbers used in the present invention refer to different subtilases depending on which subgroup the subtilase belongs to.

As mentioned above the alkaline subtilases KP43, KP1790, KP9860, Y, SD-521 and E1 belong to the JP170 subgroup, based on sequence homology. Due to the extensive homology only subtilase Ya (SEQ ID NO: 2) and SD-521 (SEQ ID NO: 3) are in FIG. 1 aligned with JP170 (SEQ ID NO: 1). The JP170 subtilase (SEQ ID NO: 1), Y subtilase (SEQ ID NO: 2) and SD-521 subtilase (SEQ ID NO: 3) are numbered according to SEQ ID NO:1, SEQ ID NO:2 and SEQ ID NO:3, respectively.

The invention, however, is not limited to variants of these particular subtilases but extends to parent subtilases, especially of the JP170 type, containing amino acid residues at positions which are "equivalent" to the particular identified residues in the JP170 subtilase (SEQ ID NO: 1).

A residue (amino acid) position of a JP170 type subtilase is equivalent to a residue (position) of the JP170 subtilase (SEQ ID NO: 1), if it is either homologous (i.e., corresponding in position in either primary or tertiary structure) or analogous to a specific residue or portion of that residue in the JP170 subtilase (SEQ ID NO: 1)(i.e., having the same or similar functional capacity to combine, react, or interact chemically).

In order to establish homology to primary structure, the amino acid sequence of a precursor protease is directly compared to the JP170 subtilase (SEQ ID NO: 1) primary sequence by aligning the amino acid sequence of an isolated or parent wild type enzyme with a suitable well-known (standard) enzyme of the same group or class of enzymes to define a frame of reference. This type of numbering has been used in numerous patent applications relating to subtilisins of the I-S1 and I-S2 subgroups with subtilisin BPN' (SEQ ID NO: 4) as the standard subtilisin.

If nothing else is indicated herein, in the present instance the JP170 subtilase (SEQ ID NO: 1) has been chosen as standard.

In order to establish homology to the tertiary structure (3D structure) of JP170 (SEQ ID NO: 1), the 3D structure based alignment in FIG. 1 has been provided. By using this alignment the amino acid sequence of a precursor JP170 type subtilase may be directly correlated to the JP170 (SEQ ID NO: 1) primary sequence. For a novel JP170 type subtilase, the (3D based) position corresponding to a position in JP170 (SEQ ID NO: 1) is found by i) identifying the JP170 type subtilase from the alignment of FIG. 1 that is most homologous to the novel sequence,
ii) aligning the novel sequence with the sequence identified to find the corresponding position in the JP170 type subtilase (SEQ ID NO: 1) from FIG. 1, and
iii) establishing from FIG. 1 the corresponding position in JP170 (SEQ ID NO: 1).

For comparison and finding the most homologous sequence the GAP program from GCG package as described below are used.

The alignment can as indicated above be obtained by the GAP routine of the GCG package version 8 to number the variants using the following parameters: gap creation penalty=3 and gap extension penalty=0.1 and all other parameters kept at their default values.

The alignment may define a number of deletions and insertions in relation to the sequence of JP170 (SEQ ID NO: 1). In the alignment deletions are indicated by asterixes (*) in the referenced sequence, and the referenced enzyme will be considered to have a gap at the position in question. Insertions are indicated by asterixes (*) in the JP170 sequence (SEQ ID NO: 1), and the positions in the referenced enzyme are given as the position number of the last amino acid residue where a corresponding amino acid residue exists in the standard enzyme with a lower case letter appended in alphabetical order, e.g. 82a, 82b, 82c, 82d.

In case the referenced enzyme contains a N- or C-terminal extension in comparison to JP170 (SEQ ID NO: 1); an N-terminal extension is given the position number 0a, 0b, etc. in the direction of the N-terminal; and a C-terminal extension will be given either the position number of the C-terminal amino acid residue of JP170 (SEQ ID NO: 1) with a lower case letter appended in alphabetical order, or simply a continued consecutive numbering.

Thus for comparisons JP170 type subtilases are numbered by reference to the positions of the JP170 subtilase (SEQ ID NO: 1) as provided in FIG. 1. The position is then indicated as "corresponding to JP170".

Subtilases belonging to the BPN' subgroup refers to the positions of Subtilisin Novo (BPN') from *B. amyloliquefaciens* (SEQ ID NO:4).

Subtilases belonging to the TY145 subgroup refers to the positions of the TY145 subtilase (SEQ ID NO:7), see also PCT/DK2004/000066.

DETAILED DESCRIPTION OF THE INVENTION

Despite the great homology of the subtilases described above the inventors of the present invention have elucidated the three-dimensional structure of JP170, SEQ ID NO:1 by X-ray crystallography and found that there are several differences between this and the three-dimensional structure of BPN' (SEQ ID NO: 4). The inventors of the present invention have further compared the sequence homology of subtilases belonging to the Subtilisin subgroup. This is shown in FIG. 3 of the present invention.

On the basis of this comparison the inventors of the present invention suggest to divide the Subtilisin subgroup so that the JP170 type subtilases become a separate subgroup in addition to the subgroups of BPN' subtilases and TY145 subtilases PCT/DK2004/000066.

JP170 Type Subtilases

The term "JP170 subtilase" or "JP170 type subtilase" should in the context of the present invention be understood as a subtilase belonging to the Subtilisin group according to Siezen et al. Protein Science 6 (1997) 501-523 and which has at least 58% homology to JP170, SEQ ID NO:1. In particular a JP170 type subtilase may have at least 60% homology to SEQ ID NO:1, such as at least 65%, at least 70%, at least 75%, at least 80%, at least 85%, at least 90%, at least 91%, at least 92%, at least 93%, at least 94%, at least 95%, at least 96%, at least 97%, at least 98% or at least 99% homology to JP170, i.e. to SEQ ID NO:1. Thus, among others the alkaline proteases KP43, KP1790, KP9860, Protease Ya, Protease E-1 and SD-521 are subtilases belonging to the JP170 subgroup of subtilases.

A JP170 subtilase suitable for the purpose described herein may be a subtilase homologous to the three-dimensional structure of JP170 (SEQ ID NO: 1), i.e. it may be homologous to the three-dimensional structure defined by the structure coordinates in Appendix 1.

As it is well-known to a person skilled in the art that a set of structure coordinates for a protein or a portion thereof is a relative set of points that define a shape in three dimensions, it is possible that an entirely different set of coordinates could define an identical or a similar shape. Moreover, slight variations in the individual coordinates may have little or no effect on the overall shape.

These variations in coordinates may be generated because of mathematical manipulations of the structure coordinates. For example, the structure coordinates of JP170 (SEQ ID NO: 1) (Appendix 1) may be manipulated by crystallographic permutations of the structure coordinates, fractionalization of the structure coordinates, integer additions or subtractions to sets of the structure coordinates, inversion of the structure coordinates or any combination of the above. Alternatively, said variations may be due to differences in the primary amino acid sequence.

If such variations are within an acceptable standard error, such as 0.8 Å, as compared to the structure coordinates of Appendix 1, said three-dimensional structure is within the context of the present invention to be understood as being homologous to the structure of Appendix 1. The standard error may typically be measured as the root mean square deviation of e.g. conserved backbone residues, where the term "root mean square deviation" (RMS) means the square root of the arithmetic mean of the squares of the deviations from the mean.

As it is also well-known to a person skilled in the art that within a group of proteins which have a homologous structure there may be variations in the three-dimensional structure in certain areas, sub-structures or domains of the structure, e.g. loops, which are not or at least only of a small importance to the functional domains of the structure, but which may result in a big root mean square deviation of the conserved residue backbone atoms between said structures.

Thus it is well known that a set of structure coordinates is unique to the crystallised protein. No other three dimensional structure will have the exact same set of coordinates, be it a homologous structure or even the same protein crystallised in a different manner. There are natural fluctuations in the coordinates. The overall structure and the inter-atomic relationship can be found to be similar. The similarity can be discussed in terms of root mean square deviation of each atom of a structure from each "homologous" atom of another structure. However, only identical proteins have the exact same number of atoms. Therefore, proteins having a similarity below 100% will normally have a different number of atoms, and thus the root mean square deviation can not be calculated on all atoms, but only the ones that are considered "homologous". A precise description of the similarity based on the coordinates is thus difficult to describe and difficult to compute for homologous proteins. Regarding the present invention, similarities in 3D structure of different subtilases can be described by the content of homologous structural elements, and/or the similarity in amino acid or DNA sequence. For sequences having no deletions or insertions a RMS for the CA carbon atoms can be calculated.

Optionally a JP170 type subtilase is further characterised as comprising the following structural characteristics:
a) a twisted beta-sheet with 7 strands,
b) six alpha helices,
c) at least three ion-binding sites, and not comprising the Strong and Weak ion-binding site of the BPN' like subtilases Further the isolated nucleic acid sequence encoding a JP170 subtilase of the invention hybridizes with a complementary strand of a nucleic acid sequence encoding the amino acid sequence of SEQ ID NO:1 preferably under low stringency conditions, at least under medium stringency conditions, at least under medium/high stringency conditions, at least under high stringency conditions, at least under very high stringency conditions.

Suitable experimental conditions for determining hybridization at low, medium, or high stringency conditions between a nucleotide probe and a homologous DNA or RNA sequence involves presoaking of the filter containing the DNA fragments or RNA to hybridize in 5×SSC (Sodium chloride/Sodium citrate, Sambrook et al. 1989) for 10 min, and prehybridization of the filter in a solution of 5×SSC, 5×Denhardt's solution (Sambrook et al. 1989), 0.5% SDS and 100 μg/ml of denatured sonicated salmon sperm DNA (Sambrook et al. 1989), followed by hybridization in the same solution containing a concentration of 10 ng/ml of a random-primed (Feinberg, A. P. and Vogelstein, B. (1983) *Anal. Biochem.* 132:6-13), $^{32}$P-dCTP-labeled (specific activity >1×10$^9$ cpm/μg) probe for 12 hours at ca. 45° C. The filter is then washed twice for 30 minutes in 2×SSC, 0.5% SDS at least * 55° C. (low stringency), more preferably at least 60° C. (medium stringency), still more preferably at least 65° C. (medium/high stringency), even more preferably at least 70° C. (high stringency), and even more preferably at least 75° C. (very high stringency).

BPN' Subtilases

A BPN' subtilase or BPN' type subtilase is in the context of the present invention to be understood as a subtilase belonging to the Subtilisin group according Siezen et al. Siezen et al. Protein Science 6 (1997) 501-523 and which has at least 61% homology to SEQ ID NO:4. In particular a BPN' subtilase may have at least 65%, such as at least 70%, at least 75%, at least 80%, at least 85%, at least 90%, at least 91%, at least 92%, at least 93%, at least 94%, at least 95%, at least 96%, at least 97%, at least 98% or at least 99% homology to BPN', i.e. to SEQ ID NO:4.

Further the isolated nucleic acid sequence encoding a BPN' subtilase of the invention hybridizes with a complementary strand of the nucleic acid sequence encoding the amino acid sequence of SEQ ID NO:4 preferably under low stringency conditions, at least under medium stringency conditions, at least under medium/high stringency conditions, at least under high stringency conditions, at least under very high stringency conditions.

In one embodiment of the present invention a BPN' subtilase suitable for the purpose described herein may be a subtilase homologous to the three-dimensional structure of BPN' as defined by the structure coordinates given in PDB Nos. 1SBT and 1GNS (Protein Data Bank), or one of the several other structures of BPN' that are accessible from the Protein Data Bank. Variations between homologous structures may occur for several reasons as described above. Thus a BPN' subtilase within the context of the present invention is to be understood as any subtilase having the structural characteristics pertaining to the BPN' subtilases as described above, and in addition such subtilases do preferably not have further structural characteristics which are not present in the BPN' subtilases as described herein. In the context of the present invention a BPN' type subtilase has two ion-binding sites. A BPN' like subtilase may, in the context of the present invention, belong to branch I-S of the subtilisins i.e. to branch I-S1, the "true" subtilisins or I-S2, the highly alkaline proteases (Siezen et al., *Protein Engng.* 4 (1991) 719-737).

Examples of BPN' type subtilases include the subtilisin 309 i.e. (SEQ ID NO: 8)(PDB NO:1SVN, SAVINASE®, NOVOZYMES A/S) and subtilisin Carlsberg (ALCALASE®, NOVOZYMES A/S), among others.

In connection with FIG. 1 of R. J. Siezen and J. A. M Leunissen (Protein science, Vol. 6 (3), pp. 501-523, 1997) page 502 a structure of subtilases is described as: A subtilase consists of 6-8 helices, 11 strands of which 7 are central in a twisted beta-sheet. Two ion-binding sites are mentioned, the so called "Strong" and "Weak" calcium-binding sites. It was later discovered that for some structures (subtilisin DY PDB no. 1BH6, 1998), the Weak calcium-binding site was shown to be a Na (sodium) binding site when the calcium concentration in the crystallization medium was low. Thus, in the following we refer to ion-binding sites instead of calcium-binding sites.

TY145 Subtilases

A TY145 subtilase or TY145 type subtilase is in the context of the present invention to be understood as a subtilase which has at least 63% homology to SEQ ID NO:7. In particular said TY145 subtilase may have at least 65%, such as at least 70%, at least 74%, at least 80%, at least 83%, at least 90%, at least 91%, at least 92%, at least 93%, at least 94%, at least 95%, at least 96%, at least 97%, at least 98% or at least 99% homology to TY145, i.e. to SEQ ID NO:7.

In one embodiment of the present invention a TY145 subtilase suitable for the purpose described herein may be a subtilase homologous to the three-dimensional structure of TY145 as defined by the structure coordinates given in PCT/DK2004/000066. Variations between homologous structures may occur for several reasons as described above. Thus a TY145 subtilase within the context of the present invention is to be understood as any subtilase having the structural characteristics pertaining to the TY145 subtilases as described above, and in addition such subtilases do preferably not have further structural characteristics which are not present in the TY145 subtilases as described herein.

Typically a TY145 subtilase further comprises the following structural characteristics:
a) a twisted beta-sheet with 7 strands,
b) six alpha helices,
c) at least three ion-binding sites, wherein the Strong ion-binding site of the BPN' type subtilases is not present, Examples of subtilases of the TY145 type include the TY145 subtilase, the psychrophilic subtilisin protease S41 derived from the Antarctic *Bacillus* TA41, herein also called TA41 subtilase (Davail S et al., 1994, J. Biol. Chem., 269, 17448-17453), and the psychrophilic subtilisin protease S39 derived from the Antarctic *Bacillus* TA39, herein also called TA39 subtilase (Narinx E et al., 1997, Protein Engineering, 10 (11), 1271-1279).

Three-Dimensional Structure of JP170 Subtilases

The JP170 subtilase (SEQ ID NO: 1) was used to elucidate the three-dimensional structure forming the basis for the present invention.

The structure of JP170 (SEQ ID NO: 1) was solved in accordance with the principle for x-ray crystallographic methods, for example, as given in X-Ray Structure Determination, Stout, G. K. and Jensen, L. H., John Wiley & Sons, Inc. NY, 1989.

The structural coordinates for the solved crystal structure of JP170 (SEQ ID NO: 1) are given in standard PDB format (Protein Data Bank, Brookhaven National Laboratory, Brookhaven, Conn.) as set forth in Appendix 1. It is to be understood that Appendix 1 forms part of the present application. In the context of Appendix 1, the following abbreviations are used: CA refers to c-alpha (carbon atoms) or to calcium ions, (however to avoid misunderstandings we normally use the full names "c-alpha atoms" and "calcium" or "ion" in the present specification). Amino acid residues are given in their standard three-letter code. The attached structural coordinates contain the protease structure, and an inhibitor structure CI2 as well as water molecules. The protease coordinates has a chain identification called A, whereas the CI2 inhibitor is called B, the calcium ions are called C, and the water is W. In the following the positions of the mentioned residues refer to the sequence of JP170 as disclosed in SEQ ID NO:1.

The JP170 structure consists of two domains, a catalytic domain and a C-terminal domain.

The structure of the catalytic domain shows the same overall fold as found in the S8 family of subtilisins. The structure comprises a twisted beta-sheet with 7 strands arranged in the following sequential order S2, S3, S1, S4, S5, S6, S7.

There are six alpha helices in the catalytic domain structure of which number H1 contains residues 9-17 (SEQ ID NO: 1), H2 contains residues 68-76 (SEQ ID NO: 1), H3 contains residues 110-119 (SEQ ID NO: 1), H4 contains residues 139-150 (SEQ ID NO: 1), H5 contains residues 253-273 (SEQ ID NO: 1) and H6 contains residues 281-291 (SEQ ID NO: 1).

The C-terminal domain comprises a strand motif, a so called "beta sandwich" consisting of sheets a and b. The sheet in this domain is combined of strands in an anti-parallel fashion, whereas the strand in the catalytic domain is combined in parallel. The sequential order of the strands can be denoted as: S1a-S1b-S3a-S3b-S4b-S4a-S2b-S2a with the beta sandwich organised as to the two sheets S1a, S3a, S4a, S2a and S1b, S3b, S4b, S2b.

The JP170 subtilases were found to lack the well-known Strong and Weak ion-binding sites of the BPN' subtilases. However, the JP170 subtilases have three ion-binding sites which are not present in the BPN' subtilisin structures. This can be seen in the structural alignment presented in FIG. 2. These three ion-binding sites are hereinafter referred to as Site 1, which is placed in the catalytic domain, and Site 2 and 3 which are placed in the non-catalytic C-terminal domain.

Thus in relation to the atomic coordinates disclosed in Appendix 1, the ion-binding sites of JP170 i.e. (SEQ ID NO: 1) are located at:
Site 1—calcium atom named A601 CA
Site 2—calcium atom named A603 CA, and
Site 3—calcium atom named A602 CA in the PDB table (Appendix 1).

The position of an ion-binding site can be defined by the distance to four specific atoms in the core structure. The distance from the ion-binding site to the c-alpha atoms of the three active site residues has been chosen. Throughout the subtilases the residues Ser, His and Asp in the active site are highly conserved. In JP170 (SEQ ID NO: 1) they are Asp30, His68 and Ser254. The fourth distance chosen is the distance to the c-alpha atom of the amino acid residue coming first after the active site serine residue in the sequence (herein after called "next to Ser"); in the 3D structure of JP170 (SEQ ID NO: 1) it is Met255.

In a preferred embodiment of the present invention, the distance between:
a) ion-binding site 1 and
   i) Asp c-alpha atom is 26.70-28.70 Å,
   ii) His c-alpha atom is 22.10-24.10 Å,
   iii) Ser c-alpha atom is 16.95-18.95 Å,
   iv) next to Ser c-alpha atom is 15.30-17.30 Å,
b) ion-binding site 2 and
   i) Asp c-alpha atom is 33.50-35.50 Å,
   ii) His c-alpha atom is 37-39 Å,
   iii) Ser c-alpha atom is 29.40-31.40 Å,
   iv) next to Ser c-alpha atom is 30.70-32.70 Å,
c) ion-binding site 3 and
   i) Asp c-alpha atom is 41.50-43.50 Å,
   ii) His c-alpha atom is 42.90-44.90 Å,
   iii) Ser c-alpha atom is 34.50-36.50 Å,
   iv) next to Ser c-alpha atom is 35-37 Å.

Below the specific distances between the four chosen c-alpha atoms and the three ion binding sites of the JP170 subtilase (SEQ ID NO: 1); and the distances between the ion binding sites are given in Å:

|  | site 1 | site 2 | site 3 |
|---|---|---|---|
| Asp30 (SEQ ID NO: 1) | 27.69 | 34.49 | 42.48 |
| His68 (SEQ ID NO: 1) | 23.12 | 38.03 | 43.87 |
| Ser254 (SEQ ID NO: 1) | 17.95 | 30.41 | 35.51 |
| Met255 (SEQ ID NO: 1) | 16.34 | 31.68 | 36.02 |
| site 1 | 0 | 35.29 | 32.92 |
| site 2 | 35.29 | 0 | 14.08 |
| site 3 | 32.92 | 14.08 | 0 |

However, these distances may vary from one subtilase to the other. The present distances are given with a calcium ion in the structure. If a sodium ion was bound instead the distances would be shifted a little bit. Generally the distances can vary ±0.80 Å, preferably ±0.70 Å, ±0.60 Å, ±0.50 Å, ±0.40 Å, or most preferably ±0.30 Å.

Further, in the JP170 like subtilases, the peptide structure circumscribing ion-binding site 1 up to a distance of 10 Å from the metal ion is composed of the amino acid residues placed in positions 183-189 (SEQ ID NO: 1), 191-204 (SEQ ID NO: 1) and 224-225 (SEQ ID NO: 1).

The peptide structure circumscribing ion-binding site 2 up to a distance of 10 Å from the metal ion is composed of residues 378-393 (SEQ ID NO: 1).

The peptide structure circumscribing ion-binding site 3 up to a distance of 10 Å from the metal ion is composed of residues 348, 350, 352, 363-370, 380-383, 391-400 and 414-420 (SEQ ID NO: 1).

Comparison to the I-S1 and I-S2 Subgroups (BPN' Like Subtilases)

In comparison to the BPN' like subtilase structures the structure of the JP170 like subtilases can be divided into a "core subtilase-like" region, an "intermediate" region and a "nonhomologous" region.

The active site can be found in the core subtilase-like region, which is structurally closely related to the BPN' structures. The core subtilase-like region is composed of residues 17-34, 197-209 and 216-232 (SEQ ID NO: 1), and contains the alpha-helix H3 and the central alpha-helix H5 in which the active site serine residue is situated in the N-terminal part. The core subtilase-like region has an RMS lower than 1.2.

Outside the core subtilase-like region the structure of the JP170 like subtilase differs from the BPN' structures to a greater extent.

The intermediate region consists of residues 42-46, 150-186, 245-272 and 278-296 (SEQ ID NO: 1). The intermediate region has an RMS bigger than 1.2 and less than 1.8. The relationships between the three-dimensional structure and functionality are potentially difficult to predict in this region of the JP170 like subtilases.

The nonhomologous region consists of residues 1-16, 35-41, 47-149, 187-196, 210-215, 233-244, 273-277 and 297-316 (SEQ ID NO: 1). The nonhomologous region has a RMS higher than 1.8. The relationships between the three-dimensional structure and functionality are very difficult to predict in this region of the JP170 like subtilases.

Many loops in the 3D structure of the JP170 like subtilases differ significantly from the BPN' type structures, both in length and in content of amino acid residues. The following loops or protein sequence stretches of JP170 (SEQ ID NO: 1) are compared to Savinase (SEQ ID NO: 8) (BPN' numbering in parenthesis, (cf. FIG. 4)):

```
G32-H43    (SEQ ID NO: 1)  (G34-H39   (SEQ ID NO: 8))
E44-Y54    (SEQ ID NO: 1)  (P40-A48   (SEQ ID NO: 8))
G57-G67    (SEQ ID NO: 1)  (V51-G63   (SEQ ID NO: 8))
N79-N82    (SEQ ID NO: 1)  (I75-V81   (SEQ ID NO: 8))
I96-P107   (SEQ ID NO: 1)  (V95-S105  (SEQ ID NO: 8))
A108-S119  (SEQ ID NO: 1)  (106-N117  (SEQ ID NO: 8))
A131-Y137  (SEQ ID NO: 1)  (S128-S132 (SEQ ID NO: 8))
T138-D152  (SEQ ID NO: 1)  (A133-G146 (SEQ ID NO: 8))
E162-I169  (SEQ ID NO: 1)  (S156-I165 (SEQ ID NO: 8))
G173-T180  (SEQ ID NO: 1)  (A169-A176 (SEQ ID NO: 8))
E185-N199  (SEQ ID NO: 1)  (D181-N184 (SEQ ID NO: 8))
G208-D218  (SEQ ID NO: 1)  (G193-D197 (SEQ ID NO: 8))
S232-K246  (SEQ ID NO: 1)  (G211-T213 (SEQ ID NO: 8))
D294-N303  (SEQ ID NO: 1)  (S256-L262 (SEQ ID NO: 8))
```

The loops N79-N82 (I75-V81) and G208-D218 (G193-D197) are in contact with a ion-binding site in Savinase (SEQ ID NO: 8), but not in JP170 (SEQ ID NO: 1). Similarly the loop E185-N199 (D181-N184) is in contact with a ion-binding site in JP170 (SEQ ID NO: 1), but not in Savinase (SEQ ID NO: 8). This knowledge opens for possibilities of adding or removing ion-binding sites to subtilases of the JP170 and BPN' like types.

A good example of the difference is the loop S232-K246 in JP170 (SEQ ID NO: 1) which has 15 residues compared to the corresponding BPN' type loop G211-T213 (SEQ ID NO: 8), which has only three residues. In the JP170 like subtilases, the loop folds back to the substrate binding site, especially the P' parts of the substrate binding site. The loop is situated close to the substrate as illustrated by the CI2 inhibitor bound in the 3D structure attached (Appendix 1).

The location of loop S232-K246 in JP170 (SEQ ID NO: 1) can be described in relation to the four specific residues as described above. The distance from the CA atom of residue W240 in the loop to the CA atoms of the active site residues are:

| Residue | H68 (SEQ ID NO: 1) | D30 (SEQ ID NO: 1) | S254 (SEQ ID NO: 1) | M255 (SEQ ID NO: 1) |
|---|---|---|---|---|
| Distance, Å | 11.45 | 18.51 | 13.06 | 11.94 |

As mentioned above, distances like these can vary ±0.80 Å, preferably ±0.70 Å, ±0.60 Å, +0.50 Å, ±0.40 Å, or most preferably ±0.30 Å.

Furthermore, distances from the residues of JP170 loop S232-K246 (SEQ ID NO: 1) to atoms of the CI2 inhibitor can be calculated. These distances are:
from CA atom of W240 to CA atom of R62 in CI2 is 7.49 Å,
from CA atom of F239 to CA atom of R62 in CI2 is 8.39 Å,
from CA atom of S238 to CA atom of R62 in CI2 is 8.42 Å,
from CA atom of S237 to CA atom of R62 in CI2 is 9.44 Å,
from CA atom of S238 to CA atom of E60 in CI2 is 9.42 Å.

The distances from JP170 (SEQ ID NO: 1) active site residue S254 (SEQ ID NO: 1) to atoms of the CI2 inhibitor, as placed in the 3D coordinates of Appendix 1, are:
from CA atom of S254 to CA atom of E60 in CI2 is 5.25 Å,
from CA atom of S254 to CA atom of R62 in CI2 is 11.55 Å,
from CA atom of S254 to CA atom of T58 in CI2 is 7.06 Å,
from CA atom of S254 to CA atom of M59 in CI2 is 4.71 Å.

The distances can vary ±0.80 Å, preferably ±0.70 Å, ±0.60 Å, ±0.50 Å, ±0.40 Å, or most preferably ±0.30 Å.

A preferred JP170 like subtilase variant has a deletion in the region S232-K246 (SEQ ID NO: 1), and the subsequent insertion of one or more residues to partly or completely remove the loop. Preferred variants comprises the deletion of L233-S245+insertion of Asn (SEQ ID NO: 1), deletion of L233-D244+insertion of Gly or deletion of S232-D244+insertion of Gly (SEQ ID NO: 1).

Similar considerations can be made in respect of differences to the TY145 structure.

Homology Building of JP170, BPN' and TY145 Subtilases

A model structure of a JP170 type subtilase, a BPN' type subtilase or a TY145 type subtilase can be built using the Homology program or a comparable program, e.g., Modeller (both from Molecular Simulations, Inc., San Diego, Calif.). The principle is to align the amino acid sequence of a protein for which the 3D structure is known with the amino acid sequence of a protein for which a model 3D structure has to be constructed. The structurally conserved regions can then be built on the basis of consensus sequences. In areas lacking homology, loop structures can be inserted, or sequences can be deleted with subsequent bonding of the necessary residues using, e.g., the program Homology. Subsequent relaxing and optimization of the structure should be done using either Homology or another molecular simulation program, e.g., CHARMm from Molecular Simulations.

Methods for Designing JP170, BPN', and TY145 Subtilase Variants

Comparisons of the molecular dynamics of different proteins can give a hint as to which domains are important or connected to certain properties pertained by each protein.

Thus the present invention relates to a method for constructing a variant of a parent subtilase, wherein the variant has at least one altered property as compared to said parent subtilase, which method comprises:

a) analyzing the three-dimensional structure of the parent subtilase to identify, on the basis of an evaluation of structural considerations in relation to a JP170 (SEQ ID NO: 1) three dimensional structure, at least one amino acid residue or at least one structural region of the subtilase, which is of relevance for altering said property;
b) modifying the DNA of the polynucleotide encoding the parent to construct a polynucleotide encoding a variant subtilase, which in comparison to the parent subtilase, has been modified by deletion, substitution or insertion of the amino acid residue or structural part identified in i) so as to alter said property;
c) expressing the variant subtilase in a suitable host, and
d) testing the resulting subtilase variant for said property.

More specifically the invention relates to a method of producing a subtilase variant, wherein the variant has at least one altered property as compared to a parent subtilase, which method comprises:
a) producing a model structure of the parent subtilase on the three-dimensional structure of BPN' (SEQ ID NO: 4), TY145 (SEQ ID NO: 7) or JP170 (SEQ ID NO: 1); or producing an actually determined three-dimensional structure of the parent subtilase,
b) comparing the model or actual three-dimensional structure of the parent subtilase to the JP170 (SEQ ID NO: 1) structure by superimposing the structures through matching the CA, CB, C, O, and N atoms of the active site residues,
c) identifying on the basis of the comparison in step b) at least one structural part of the parent subtilase, wherein an alteration in said structural part is predicted to result in an altered property;
d) modifying the nucleic acid sequence encoding the parent subtilase to produce a nucleic acid sequence encoding at least one deletion or substitution of one or more amino acids at a position corresponding to said structural part, or at least one insertion of one or more amino acid residues in positions corresponding to said structural part;
e) performing steps c) and d) iteratively N times, where N is an integer with the value of one or more;
f) preparing the variant resulting from steps a)-e);
g) testing the properties of said variant; and
h) optionally repeating steps a)-g) recursively; and
i) selecting a subtilase variant having at least one altered property as compared to the parent subtilase.
j) expressing the modified nucleic acid sequence in a host cell to produce the variant subtilase;
k) isolating the produced subtilase variant;
l) purifying the isolated subtilase variant and
m) recovering the purified subtilase variant.

The present invention thus generally relates to the use of the JP170 (SEQ ID NO: 1) structure as provided herein for the identification of desired modifications in subtilases of any of the three subtilisin types, the BPN' types (I-S1 and I-S2 subgroups), the TY145 types and the JP170 types through modelling the 3-D structure of a parent subtilase to the type it belongs to and subsequent comparison thereof to the JP170 3-D structure (SEQ ID NO: 1), or in instances where the 3-D structure of the parent subtilase is actually known by comparison thereof to the JP170 3-D structure (SEQ ID NO: 1).

Based on this comparison at least one residue in the parent subtilase is selected for modification by substitution, deletion or insertion in order to provide a subtilase variant with altered properties in comparison to the parent subtilase.

In one embodiment the parent subtilase may therefore belong to the sub-group I-S1, preferably selected from the group consisting of ABSS168, BASBPN, BSSDY, and BLSCAR, or functional variants thereof having retained the characteristic of sub-group I-S1.

In another embodiment the parent subtilase belongs to the sub-group I-S2, preferably selected from the group consisting of BLS147, BLS309, BAPB92, and BYSYAB, or functional variants thereof having retained the characteristic of sub-group I-S2.

In a further embodiment the parent subtilase belongs to the TY145 type subgroup, preferably selected from the group comprising TY145, protease S41 also called TA41 protease S39 also called TA39 subtilase, etc.

Specifically the parent subtilase belongs to the JP170 type subgroup, preferably selected from the group comprising JP170, KP43, KP9860, Protease E-1, Protease Ya, Protease SD-521, etc.

A further embodiment of the invention relates to a method of producing a JP170 type subtilase variant, wherein the variant has at least one altered property as compared to a parent subtilase, which method comprises:
a) producing a model structure of the parent JP170 type subtilase on the three-dimensional structure of JP170 (SEQ ID NO: 1); or producing an actually determined three-dimensional structure of the parent subtilase,
b) comparing the model or actual three-dimensional structure of the parent JP170 type subtilase to the BPN' or TY145 structure by superimposing the structures through matching the CA, CB, C, O, and N atoms of the active site residues,
c) identifying on the basis of the comparison in step b) at least one structural part of the parent JP170 type subtilase, wherein an alteration in said structural part is predicted to result in an altered property;
d) modifying the nucleic acid sequence encoding the parent JP170 type subtilase to produce a nucleic acid sequence encoding at least one deletion or substitution of one or more amino acids at a position corresponding to said structural part, or at least one insertion of one or more amino acid residues in positions corresponding to said structural part;
e) performing steps c) and d) iteratively N times, where N is an integer with the value of one or more;
f) preparing the JP170 type subtilase variant resulting from steps a)-e);
g) testing the properties of said variant; and
h) optionally repeating steps a)-g) recursively; and
i) selecting a JP170 type subtilase variant having at least one altered property as compared to the parent subtilase.
j) expressing the modified nucleic acid sequence in a host cell to produce the variant subtilase;
k) isolating the produced JP170 type subtilase variant;
l) purifying the isolated subtilase variant and
m) recovering the purified subtilase variant.

The invention also comprises the protease variants produced by the above methods.

Stability—Alteration of Ion-binding Sites

As described above the three-dimensional structure of JP170 subtilases (SEQ ID NO: 1) as provided in Appendix 1 indicates the presence of three ion-binding sites not present in the BPN' subtilisin structures, thus lacking the Strong and Weak ion-binding site of the BPN' subtilases. Stability of ion-binding sites is important for the functionality of the enzyme. Therefore alterations of the ion-binding sites are likely to result in alterations of the stability of the enzyme.

Improved Stability

Stabilisation of a JP170 subtilase may possibly be obtained by alterations in the positions close to the ion-binding sites.

Thus in one embodiment of the method of the invention step (c) above identifies amino acid residue positions located at a distance of 10 Å or less to the ion-binding site of the JP170 type parent, preferably positions located at a distance of 6 Å or less.

Thus a preferred variant of the present invention has a modification in one or more of the positions located at a distance of 10 Å to the ion-binding sites of JP170 (SEQ ID NO:1). These positions are:

| Site 1: | 183-189 | (i.e. positions 183, 184, 185, 186, 187, 188, 189) (SEQ ID NO: 1), |
| --- | --- | --- |
| | 191-204 | (i.e. positions 191, 192, 193, 194, 195, 196, 197, 198, 199, 200, 201, 202, 203, 204) (SEQ ID NO: 1), |
| | 224-225 | (SEQ ID NO: 1); |
| Site 2: | 378-393 | (i.e. positions 378, 379, 380, 381, 382, 383, 384, 385, 386, 387, 388, 389, 390, 391, 392, 393) (SEQ ID NO: 1); |
| Site 3: | 348, 350, 352 | (SEQ ID NO: 1), |
| | 363-370 | (i.e. positions 363, 364, 365, 366, 367, 368, 369, 370) (SEQ ID NO: 1), |
| | 380-383 | (i.e. positions 380, 381, 382, 383) (SEQ ID NO: 1), |
| | 391-400 | (i.e. positions 391, 392, 393, 394, 395, 396, 397, 398, 399, 400), (SEQ ID NO: 1) |
| | 414-420 | (i.e. positions 414, 415, 416, 417, 418, 419, 420) (SEQ ID NO: 1). |

Corresponding positions in other JP170 type subtilases may be identified as disclosed above or by using FIG. 1 herein.

In detergent compositions calcium chelaters contribute to removal of calcium from the subtilases with subsequent inactivation of the enzyme as the result. To decrease the inactivation due to calcium removal of e.g. calcium chelaters variants with improved calcium stability was constructed.

Preferred variants stabilised in ion-binding site 1 are S193Q,Y (SEQ ID NO: 1); H200D,N (SEQ ID NO: 1) and H200D,N+D196N (SEQ ID NO: 1).

Preferred variants stabilised in ion-binding site 2 are N390D (SEQ ID NO: 1) and N391D (SEQ ID NO: 1), and preferred variants stabilised in ion-binding site 3 are G394N, Q,F,Y,S and W392S,N,Q (SEQ ID NO: 1).

Alteration of Thermostability

A variant with improved stability (typically increased thermostability) may be obtained by substitution with proline, introduction of a disulfide bond, altering a hydrogen bond contact, altering charge distribution, introduction of a salt bridge, filling in an internal structural cavity with one or more amino acids with bulkier side groups (in e.g. regions which are structurally mobile), substitution of histidine residues with other amino acids, removal of a deamidation site, or by helix capping.

Regions with Increased Mobility:

The following regions of JP170 have an increased mobility in the crystal structure of the enzyme, and it is presently believed that these regions can be responsible for stability or activity of JP170. Especially thermostabilisation may possibly be obtained by altering the highly mobile regions. Improvements of the enzyme can be obtained by mutation in the below regions and positions. Introducing e.g. larger residues or residues having more atoms in the side chain could increase the stability, or, e.g., introduction of residues having fewer atoms in the side chain could be important for the mobility and thus the activity profile of the enzyme.

Two methods are used extract the highly mobile regions from a 3D structure. One is a molecular dynamics calculation of the isotropic fluctuations by using the program CHARMm from MSI (Molecular Simulations Inc.), and the other is an analysis of the B-factors. The B-factors are listed in Appendix 1 and give a value to the uncertainty of determination of the location of the various atoms of the structure. The uncertainty relates to the mobility of the atoms in the molecules in the crystal lattice. This mobility reflects the thermal motion of the atoms and thus indicates possible sites for thermostabilisation of the enzyme.

Thus, by analysing the B-factors taken from the coordinate file in Appendix 1, (see "X-Ray Structure Determination, Stout, G. K. and Jensen, L. H., John Wiley & Sons, Inc. NY, 1989") the following mobile regions in the JP170 structure were determined:

| 13-18 | (i.e. positions 13, 14, 15, 16, 17, 18) (SEQ ID NO: 1), |
| --- | --- |
| 37-43 | (i.e. positions 37, 38, 39, 40, 41, 42, 43) (SEQ ID NO: 1), |
| 47-50 | (i.e. positions 47, 48, 49, 50) (SEQ ID NO: 1), |
| 57-59 | (i.e. positions 57, 58, 59) (SEQ ID NO: 1), |
| 96-103 | (i.e. positions 96, 97, 98, 99, 100, 101, 102, 103) (SEQ ID NO: 1), |
| 131-134 | (i.e. positions 131, 132, 133, 134) (SEQ ID NO: 1), |
| 152-153 | (SEQ ID NO: 1) |
| 162-166 | (i.e. positions 162, 163, 164, 165, 166) (SEQ ID NO: 1), |
| 188-195 | (i.e. positions 188, 189, 190, 191, 192, 193, 194, 195) (SEQ ID NO: 1), |
| 210 | (SEQ ID NO: 1) |
| 234-246 | (i.e. positions 234, 235, 236, 237, 238, 239, 240, 241, 242, 243, 244, 245, 246) (SEQ ID NO: 1), |
| 372-378 | (i.e. positions 372, 373, 374, 375, 376, 377, 378) (SEQ ID NO: 1), |
| 387-392 | (i.e. positions 387, 388, 389, 390, 391, 392) (SEQ ID NO: 1), |
| 406-407 | (SEQ ID NO: 1) |
| 419 | (SEQ ID NO: 1). |

Molecular dynamics simulations at 300K and 400K of JP170 provided the following highly mobile regions:

| 37-42 | (i.e. positions 37, 38, 39, 40, 41, 42) (SEQ ID NO: 1), |
| --- | --- |
| 57-60 | (i.e. positions 57, 58, 59, 60) (SEQ ID NO: 1), |
| 66-67, | (SEQ ID NO: 1) |
| 98-103 | (i.e. positions 98, 99, 100, 101, 102, 103), (SEQ ID NO: 1) |
| 107-111 | (i.e. positions 107, 108, 109, 110, 111), (SEQ ID NO: 1) |
| 188-193 | (i.e. positions 188, 189, 190, 191, 192, 193), (SEQ ID NO: 1) |
| 236-240 | (i.e. positions 236, 237, 238, 239, 240), (SEQ ID NO: 1) |
| 326-332 | (i.e. positions 326, 327, 328, 329, 330, 331, 332), (SEQ ID NO: 1) |
| 337-342 | (i.e. positions 337, 338, 339, 340, 341, 342), (SEQ ID NO: 1) |
| 355-360 | (i.e. positions 355, 356, 357, 358, 359, 360), (SEQ ID NO: 1) |
| 372-377 | (i.e. positions 372, 373, 374, 375, 376, 377), (SEQ ID NO: 1) |
| 384-388 | (i.e. positions 384, 385, 386, 387, 388), (SEQ ID NO: 1) |
| 404-411 | (i.e. positions 404, 405, 406, 407, 408, 409, 410, 411) (SEQ ID NO: 1). |

Thus, a preferred JP170 subtilase variant of the present invention has been modified in one or more of the above mentioned positions of SEQ ID NO:1. Further preferred variants comprises one or more alterations in the regions 57-60, 66-67, 107-111, 236-240, 326-332, 355-360, 372-377, 384-388, 404-411 of (SEQ ID NO: 1). Especially preferred is variant W240H,Y (SEQ ID NO: 1) and variants modified in the region 355-360 (SEQ ID NO: 1), such as variants comprising one or more of the modifications: G355 Å,S (SEQ ID NO: 1); S356T,N (SEQ ID NO: 1); T357N,Q,D,E,P (SEQ ID NO: 1); T358S (SEQ ID NO: 1); A359S,T,N,Q (SEQ ID NO: 1) and S360T,N (SEQ ID NO: 1).

Variants modified in the region 355-360 (SEQ ID NO: 1) may be produced in accordance with the method for random mutagenesis by use of the DOPE program as described herein. To obtain variants comprising 1-3 modifications in region 355-360 (SEQ ID NO: 1) one may introduce the substitutions with the following frequencies:

| wild-type | modified |
|---|---|
| 95% | 5% G355A, S (SEQ ID NO: 1) |
| 90% | 10% S356T, N (SEQ ID NO: 1) |
| 80% | 20% T357N, Q, D, E, P (SEQ ID NO: 1) |
| 90% | 10% T358S (SEQ ID NO: 1) |
| 80% | 20% A359S, T, N, Q (SEQ ID NO: 1) |
| 80% | 20% S360T, N (SEQ ID NO: 1). |

Disulfide Bonds:

A JP170 variant of the present invention with improved stability, e.g. thermostability, as compared to the parent JP170 subtilase may be obtained by introducing new inter-domain or intra-domain bonds, such as by establishing inter- or intra-domain disulfide bridges.

Thus a further aspect of the present invention relates to a method for producing a variant of a parent JP170, wherein step (c) identifies amino acid residue positions in the parent JP170 type subtilase, the modification of which may create at least one disulfide bridge by insertion of or substitution with at least one Cys residue.

The below mentioned amino acid residues identified in the amino acid sequence of SEQ ID NO:1 are considered as being suitable for cysteine replacement. With one or more of these substitutions with cysteine, disulfide bridges may possibly form in a variant of JP170. The substitutions are: G21C+A86C, V26C+A265C, G57C+G105C, G74C+A229C, Q111C+N143C, G160C+S170C, A286C+V349C, A27C+A122C, A45C+G78C, V72C+P258C, G78C+A229C, D98C+G104C, Q111C+Y147C, G135C+G167C, R142C+P354C, V144C+A178C, G182C+P217C, A183C+G223C, A195C+Y225C, F271C+P279C, A287C+A430C, A293C+T310C, E322C+S428C, S324C+A332C, S327C+P424C, D352C+N397C, G355C+T362C, G291C+S314C (SEQ ID NO: 1).

Preferred variants comprise one or more of the substitutions: G21C+A86C, V26C+A265C, G57C+G105C, G74C+A229C, Q111C+Y143C, G160C+S170C, A286C+V349C, A4C+P222C and A27C+A 117C (SEQ ID NO: 1).

Similar residues suitable for cysteine replacement in subtilases homologous with JP170 can be elucidated by finding the homologous positions in the alignment of FIG. 1. Concerning another JP170 like sequence the homologous positions suitable for cysteine replacement can be selected by aligning said JP170 like sequence with all of the sequences of FIG. 1 using the GAP analysis method as described above. The suitable residues can then be selected in accordance with the homologous positions in the most homologous of SEQ ID's NO:1, 2 and 3 which are the sequences of the subtilases aligned in FIG. 1.

Surface Charge Distribution

A variant with improved stability (typically improved thermostability) as compared to the parent subtilase may be obtained by changing the surface charge distribution of the subtilase. For example, when the pH is lowered to about 5 or below histidine residues typically become positively charged and, consequently, unfavorable electrostatic interactions on the protein surface may occur. By engineering the surface charge of the subtilase one may avoid such unfavorable electrostatic interactions that in turn lead to a higher stability of the subtilase.

Charged amino acid residues are (a) positively charged: Lys, Arg, His (pH<5), Tyr (pH>9) and Cys (pH>10) and (b) negatively charged: Asp and Glu.

Therefore, a further aspect of the present invention relates to method for constructing a variant of a parent subtilase, the method comprising:
  a) identifying, on the surface of the parent subtilase, preferably a JP170 like or a BPN' like subtilase, at least one amino acid residue selected from the group consisting of Asp, Glu, Arg, Lys and His;
  b) substituting, on the surface of the parent subtilase, at least one amino acid residue selected from the group consisting of Asp, Glu, Arg, Lys and His with an uncharged amino acid residue;
  c) optionally repeating steps a) and b) recursively;
  d) optionally, making alterations each of which is an insertion, a deletion or a substitution of an amino acid residue at one or more positions other than b);
  e) preparing the variant resulting from steps a)-d);
  f) testing the stability of said variant; and
  g) optionally repeating steps a)-f) recursively; and
  h) selecting a subtilase variant having increased stability as compared to the parent subtilase.

As will be understood by the skilled person it may also, in some cases, be advantageous to substitute an uncharged amino acid residue with an amino acid residue bearing a charge or, alternatively, it may in some cases be advantageous to substitute an amino acid residue bearing a charge with an amino acid residue bearing a charge of opposite sign. Thus, the above-mentioned method may easily be employed by the skilled person also for these purposes. In the case of substituting an uncharged amino acid residue with an amino acid residue bearing a charge the above-mentioned method may be employed the only difference being steps a) and b) which will then read:
  a) identifying, on the surface of the parent subtilase, at least one uncharged amino acid residue;
  b) substituting, on the surface of the parent subtilase, at least one uncharged amino acid residue with a charged amino acid residue selected from the group consisting of Asp, Glu, Arg, Lys and His.

Also in the case of changing the sign of an amino acid residue present on the surface of the subtilase the above method may be employed. Again, compared to the above method, the only difference being steps a) and b) which, in this case, read:
  a) identifying, on the surface of the parent subtilase, at least one charged amino acid residue selected from the group consisting of Asp, Glu, Arg, Lys and His;
  b) substituting, on the surface of the parent subtilase, at least one charged amino acid residue identified in step a) with an amino acid residue having an opposite charge.

Thus, Asp may be substituted with Arg, Lys or His; Glu may be substituted with Arg, Lys or His; Arg may be substituted with Asp or Glu; Lys may be substituted with Asp or Glu; and His may be substituted with Asp or Glu.

In order to determine the amino acid residues of a subtilase, which are present on the surface of the enzyme, the surface accessible area are measured using the DSSP program (Kabsch and Sander, *Biopolymers* (1983), 22, 2577-2637). All residues having a surface accessibilty higher than 0 0, 0.10, 0.20, 0.30, 0.35, 0.40, 0.45, 0.50, 0.55 or 0.60 are regarded a surface residue.

Among the amino acid residues found on the surface of JP170 (SEQ ID NO: 1) using the above method are N79, N316, L381, K246, K9, K313 and K83. We consider the substitutions N79D, N316D and L381D of particular interest for stabilisation by introduction of salt bridges, whereas the substitutions K246R, K9R, K313R and K83R are of particular interest for the stabilisation at high pH.

Similar substitutions may be introduced in equivalent positions of other JP170 like subtilases.

Substitution with Proline Residues

Improved thermostability of a subtilase can be obtained by subjecting the subtilase in question to analysis for secondary structure, identifying residues in the subtilase having dihedral angles φ (phi) and ψ (psi) confined to the intervals [$-90°<\phi<-40°$ and $-180°<\psi<180°$], preferably the intervals [$-90°<\phi<-40°$ and $120°<\psi<180°$] or [$-90°<\phi<-40°$ and $-50°<\psi<10°$] and excluding residues located in regions in which the subtilase is characterized by possessing α-helical or β-sheet structure.

After the dihedral angles φ (phi) and ψ (psi) for the amino acids have been calculated, based on the atomic structure in the crystalline subtilases, it is possible to select position(s) which has/have dihedral phi and psi angles favorable for substitution with a proline residue. The aliphatic side chain of proline residues is bonded covalently to the nitrogen atom of the peptide group. The resulting cyclic five-membered ring consequently imposes a rigid constraint on the rotation about the N—$C_\alpha$ bond of the peptide backbone and simultaneously prevents the formation of hydrogen bonding to the backbone N-atom. For these structural reasons, proline residues are generally not compatible with α-helical and β-sheet secondary conformations.

If a proline residue is not already at the identified position(s), the naturally occurring amino acid residue is substituted with a proline residue, preferably by site directed mutagenesis applied on a gene encoding the subtilase in question.

In the group of JP170 type subtilases proline residues can advantageously be introduced at positions 22, 44, 110, 139, 140, 166, 198, 201, 203, 231, 282, 356, 357 and 378. Accordingly, a preferred JP170 variant has one or more of the substitutions: Q22P, E44P, L110P, T139P, D140P, S166P I198P, V201P, Q203P, S231P, S282P, S356P, T357P and K378P. Especially preferred are variants comprising one or more of: E44P, Q203P and S356P.

Improved Activity of JP170 Subtilases

As mentioned, the JP170 subtilases differ greatly from the BPN' like subtilases in having a long apparently non-catalytic C-terminal. A possible truncation of JP170 is the removal of approx. 115 residues including two ion-binding sites, which can be obtained by deletion of or within the region 311-433 (SEQ ID NO: 1), which is the non-catalytic C-terminal. Preferred deletions comprises the regions 317-433 (SEQ ID NO: 1) or 315-433 (SEQ ID NO: 1). Preferably the new C-terminal will be within the region of 311-325 (SEQ ID NO: 1). Further, the deletion can be optimised with additional substitutions, such as one or more of L283N,Q; A290S,N (SEQ ID NO: 1) and W306H,Y,K (SEQ ID NO: 1).

Preferred truncations comprise:
a) deletion of region 317-433 (SEQ ID NO: 1) and the substitutions L283N+A290S+W306H (SEQ ID NO: 1),
b) deletion of region 315-433 (SEQ ID NO: 1) and the substitutions L283N+A290S+W306H (SEQ ID NO: 1).

Substrate Binding Site

The substrate binding site is identified by the residues in contact with a substrate model, such as the CI2 inhibitor. The 3D structure coordinates of the JP170 subtilase with CI2 bound in the active site are provided in Appendix 1. Without being limited to any theory, it is presently believed that binding between a substrate and an enzyme is supported by favorable interactions found within a sphere 10 Å from the substrate molecule. Examples of such favorable bonds are hydrogen bonds, strong electrostatic interaction and/or hydrophobic interactions.

The following residues of the JP170 subtilase (SEQ ID NO:1), are within a distance of 10 Å from the CI2 inhibitor which is bound to the substrate binding site. These residues are thus believed to be involved in interactions with said substrate:

| | |
|---|---|
| 29-32, | (i.e. residues 29, 30, 31, 32) (SEQ ID NO: 1) |
| 64-72, | (i.e. residues 64, 65, 66, 67, 68, 69, 70, 71, 72) (SEQ ID NO: 1) |
| 93, | (SEQ ID NO: 1) |
| 96-98, | (i.e. residues 96, 97, 98) (SEQ ID NO: 1) |
| 100-110, | (i.e. residues 100, 101, 102, 103, 104, 105, 106, 107, 108, 109, 110) (SEQ ID NO: 1) |
| 113-114, | (SEQ ID NO: 1) |
| 127-136, | (i.e. residues 127, 128, 129, 130, 131, 132, 133, 134, 135, 136) (SEQ ID NO: 1) |
| 138-141, | (i.e. residues 138, 139, 140, 141) (SEQ ID NO: 1) |
| 144, 157, 174, | (SEQ ID NO: 1) |
| 180-183, | (i.e. residues 180, 181, 182, 183) (SEQ ID NO: 1) |
| 191, 193-194, | (SEQ ID NO: 1) |
| 202-207, | (i.e. residues 202, 203, 204, 205, 206, 207) (SEQ ID NO: 1) |
| 211, | (SEQ ID NO: 1) |
| 223-226, | (i.e. residues 223, 224, 225, 226) (SEQ ID NO: 1) |
| 234-241, | (i.e. residues 234, 235, 236, 237, 238, 239, 240, 241) (SEQ ID NO: 1) |
| 249-258 | (i.e. residues 249, 250, 251, 252, 253, 254, 255, 256, 257, 258) (SEQ ID NO: 1). |

In an embodiment of the present invention a variant comprises a modification in one or more of the above mentioned positions. A preferred variant is W129L (SEQ ID NO: 1).

JP170 with Extra Ion-binding Site

The Strong ion-binding site from the BPN' subtilases can be transplanted into JP170 (or other subtilases in JP170 subgroup) by deletion of N79-N82 e.g. (SEQ ID NO: 1) and subsequent insertion of LNNSIGV (SEQ ID NO:5), followed by the substitution A45D,N and optionally the substitutions E44P,T and/or R47Q.

Removal of Ion-binding Site in JP170

By removing an ion-binding site it is possible to decrease the enzymes dependency of calcium in the media. The ion-binding sites in JP170 or other JP170 type subtilases can be removed with guidance from information about the three-dimensional structures of other related subtilases, such as a BPN' type subtilase, such as Savinase or BPN', and a TY145 type subtilase.

Removal of ion-binding site 1 can be done by deletion of N186-N199 e.g. (SEQ ID NO: 1) and subsequent insertion of at least three amino acid residues—or stated differently by the substitution of a region comprising from 3 to 6 amino acid residues for the region comprising 14 amino acid residues in positions 186 to 199 e.g. (SEQ ID NO: 1), preferably the sequence of the substituting region is SSN (SEQ ID NO:6). Preferably, but not mandatory one or both of the substitutions 17Q and V3Y is further added.

The ion-binding site 1 can be removed from a wild-type JP170 subtilase or a JP170 subtilase truncated as described above.

Subtilases Free of Ion-binding Sites

Similarly, information about the three-dimensional structures of JP170 type subtilases and TY145 type subtilases can be used to remove the Strong and Weak ion-binding sites in BPN' type subtilases, or the ion-binding sites in TY145 type subtilases may be removed on the basis of structural information about the JP170 and BPN' types of subtilases.

Using Savinase as an example, the removal can be done by altering the loops A194-L196 (weak ion-binding site) and L75-L82 (strong ion-binding site) either by a) insertion or deletion of a number of amino acid residues in the loops or b)

by deletion of the entire loop or part of the loop and subsequent insertion of a number of residues from a corresponding loop of a JP170 or TY145 like subtilase.

Preferably the ion-binding sites of Savinase can be removed by either
i) full or partial deletion of the region A194-L196 (BPN' numbers) and insertion of three or more residues chosen from JP170 positions P209-P217, and
ii) full or partial deletion of the region L75-L82 (BPN' numbers) and insertion of at least one residue chosen from TY145 positions H83-Y92
or
i) full or partial deletion of the region A194-L196 (BPN' numbers) and insertion of three or more residues chosen from JP170 positions P209-P217 and
ii) full or partial deletion of the region L75-L82 (BPN' numbers) and insertion of at least one residues chosen from JP170 positions N79-K83.

Removal of Critical Oxidation Sites

In order to increase the stability of a JP170 type subtilase protease it may be advantageous to substitute or delete critical oxidation sites, such as methionines, with other amino acid residues which are not subject to oxidation.

Accordingly, in a further embodiment the present invention relates to an RP-II protease variant, in which one or more amino acid residues susceptible to oxidation, especially methionine residues exposed to the surface of the molecule, is/are deleted or replaced with another amino acid residue less susceptible to oxidation. The amino acid residue less susceptible to oxidation may for instance be selected from the group consisting of A, E, N, Q, I, L, S and K.

Specific such variants comprises at least one of the deletions or substitutions M42{*,S,A,N,Q,K}; M85{*,S,A,N,Q,K}; M97{*,S,A,N,Q,K}; M153{*,S,A,N,Q,K}; M220{*,S,A,N,Q,K}; M250{*,S,A,N,Q,K}; and M255{*,S,A,N,Q,K} of the JP170 protease; the deletions or substitutions M42{*,S,A,N,Q,K}; M85{*,S,A,N,Q,K}; M97{*,S,A,N,Q,K}; M153{*,S,A,N,Q,K}; M250{*,S,A,N,Q,K}; and M255{*,S,A,N,Q,K} of the SD-521 and Ya proteases.

Stabilization by Modification of Asn-Gly Pairs

It is known that at alkaline pH, the side chain of Asn may interact with the NH group of a sequential neighbouring amino acid to form an isoAsp residue where the backbone goes through the Asp side chain. This will leave the backbone more vulnerable to proteolysis. The deamidation is much more likely to occur if the residue that follows is a Gly. Changing the Asn in front of the Gly or the Gly will prevent this from happening and thus improve the stability, especially as concerns thermo- and storage stability.

The invention consequently further relates to a subtilase, in which the modificatioins indicated above are either or both residues of any of the Asn-Gly sequence appearing in the amino acid sequence of the parent RP-II protease is/are deleted or substituted with a residue of a different amino acid.

The Asn and/or Gly residue may, for instance, be substituted with a residue of an amino acid selected from the group consisting of A, Q, S, P, T and Y.

More specifically, any of the Asn or Gly residues of the Asn-Gly occupying positions 66-67, 134-135 and/or 375-376 of the SD-521 and Ya protease; and positions 66-67, 134-135, 301-302 and/or 375-376 of the JP170 protease, may be deleted or substituted with a residue of an amino acid selected from the group consisting of A, Q, S, P, T and Y. (positions are indicated in relation to the JP170 protease as indicated in FIG. 1).

Specific variants of JP170 (SEQ ID NO: 1) are: N66{*,A,Q,S,P,T,Y}; G67{*,A,Q,S,P,T,Y}; N134{*,A,Q,S,P,T,Y}; G135{*,A,Q,S,P,T,Y}; N301{*,A,Q,S,P,T,Y}; G302{*,A,Q,S,P,T,Y}; N375{*,A,Q,S,P,T,Y}; and G376{*,A,Q,S,P,T,Y}; and combinations thereof, such as N66{*,A,Q,S,P,T,Y}+N134{*,A,Q,S,P,T,Y}, N66{*,A,Q,S,P,T,Y}+N301{*,A,Q,S,P,T,Y}, and N66{*,A,Q,S,P,T,Y}+N375{*,A,Q,S,P,T,Y}, etc.

Specific variants of SD-521 (SEQ ID NO: 3) and Ya (SEQ ID NO: 2) proteases are: N66{*,A,Q,S,P,T,Y}; G67{*,A,Q,S,P,T,Y}; N134{*,A,Q,S,P,T,Y}; G135{*,A,Q,S,P,T,Y}; and N375{*,A,Q,S,P,T,Y}; G376{*,A,Q,S,P,T,Y}, and combinations thereof as indicated above.

Modification of Tyrosine Residues

In relation to wash performance it has been found that the modification of certain tyrosine residues to phenylalanine provides an improved wash performance. Without being bound by any specific theory, it is believed that titration of these Tyr residues in the alkaline wash liquor has negative effects that are alleviated by replacing the Tyr residues with other residues, especially Phe or Trp, particularly Phe.

In JP170 (SEQ ID NO: 1) tyrosine residues may be modified in positions: 20, 54, 118, 137, 147, 194, 225, 247, 249, 334, 379, 388, 411, and 418.

In SD-521 (SEQ ID NO: 3) and Ya (SEQ ID NO: 2) proteases the tyrosine residues may be modified in positions: 17, 20, 54, 137, 147, 187, 243, 247, 249, 299, 319, 334, 361, 379, 386, 388, 411, and 418.

In relation to JP170 the invention thus relates to the variants: Y17{F,W}, Y20{F,W}, Y54{F,W}, Y137{F,W}, Y147{F,W}, Y187{F,W}, Y243{F,W}, Y247{F,W}, Y249{F,W}, Y299{F,W}, Y319{F,W}, Y334{F,W}, Y361{F,W}, Y379{F,W}, Y386{F,W}, Y388{F,W}, Y411{F,W}, and Y418{F,W} (SEQ ID NO: 1). Corresponding modifications are easily identified in other JP170 type subtilases.

Modification of Tryptophan Residues

In order to stabilize the protein it may be advantageous to replace or delete tryptophan residues at the surface of the protein, e.g., as described in U.S. Pat. No. 5,118,623. The tryptophan residues may advantageously be substituted for F, T, Q or G. Thus, in a further embodiment the invention relates to JP170 type subtilase variants comprising one or more of the following substitutions: For the SD-521 and Ya proteases positions 118, 129, 240, 306, 350, and 392 (SEQ ID NO: 3) and (SEQ ID NO: 2); and for the JP170 protease positions 129, 240, 306, 350, and 392 (SEQ ID NO: 1).

Thus, the invention relates to a JP170 variant comprising one or more of the following substitutions W129{F,T,Q,G}, W240{F,T,Q,G}, W306{F,T,Q,G}, W350{F,T,Q,G}, and W392{F,T,Q,G} (SEQ ID NO: 1).

Combined Modifications

The present invention also encompasses any of the above mentioned subtilase variants in combination with any other modification to the amino acid sequence thereof. Especially combinations with other modifications known in the art to provide improved properties to the enzyme are envisaged.

Methods of Preparing JP170 Like or BPN' Like Subtilase Variants

The subtilase variants, i.e. the JP170 and BPN' variants of the present invention may be produced by any known method within the art and the present invention also relates to nucleic acid encoding a subtilase variant of the present invention, a DNA construct comprising said nucleic acid and a host cell comprising said nucleic acid sequence.

In general natural occurring proteins may be produced by culturing the organism expressing the protein and subsequently purifying the protein or it may be produced by cloning a nucleic acid, e.g. genomic DNA or cDNA, encoding the protein into an expression vector, introducing said expression vector into a host cell, culturing the host cell and purifying the expressed protein.

Typically protein variants may be produced by site-directed mutagenesis of a parent protein, introduction into expression vector, host cell etc. The parent protein may be cloned from a strain producing the polypeptide or from an expression library, i.e. it may be isolated from genomic DNA or prepared from cDNA, or a combination thereof.

In general standard procedures for cloning of genes and/or introducing mutations (random and/or site directed) into said genes may be used in order to obtain a parent subtilase, or subtilase or subtilase variant of the invention. For further description of suitable techniques reference is made to Molecular cloning: A laboratory manual (Sambrook et al. (1989), Cold Spring Harbor lab., Cold Spring Harbor, N.Y.; Ausubel, F. M. et al. (eds.)); Current protocols in Molecular Biology (John Wiley and Sons, 1995; Harwood, C. R., and Cutting, S. M. (eds.)); Molecular Biological Methods for *Bacillus* (John Wiley and Sons, 1990); DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins eds (1985)); Transcription And Translation (B. D. Hames & S. J. Higgins, eds. (1984)); Animal Cell Culture (R. I. Freshney, ed. (1986)); Immobilized Cells And Enzymes (IRL Press, (1986)); A Practical Guide To Molecular Cloning (B. Perbal, (1984)) and WO 96/34946.

Further, variants could be constructed by:

Random Mutagenesis

Random mutagenesis is suitably performed either as localized or region-specific random mutagenesis in at least three parts of the gene translating to the amino acid sequence shown in question, or within the whole gene.

When the mutagenesis is performed by the use of an oligonucleotide, the oligonucleotide may be doped or spiked with the three non-parent nucleotides during the synthesis of the oligonucleotide at the positions that are to be changed. The doping or spiking may be done so that codons for unwanted amino acids are avoided. The doped or spiked oligonucleotide can be incorporated into the DNA encoding the subtilase enzyme by any published technique, using, e.g., PCR, LCR or any DNA polymerase and ligase as deemed appropriate.

Preferably, the doping is carried out using "constant random doping", in which the percentage of wild-type and modification in each position is predefined. Furthermore, the doping may be directed toward a preference for the introduction of certain nucleotides, and thereby a preference for the introduction of one or more specific amino acid residues. The doping may be made, e.g., so as to allow for the introduction of 90% wild type and 10% modifications in each position. An additional consideration in the choice of a doping scheme is based on genetic as well as protein-structural constraints. The doping scheme may be made by using the DOPE program which, inter alia, ensures that introduction of stop codons is avoided (L. J. Jensen et al. *Nucleic Acid Research,* 26, 697-702 (1998).

When PCR-generated mutagenesis is used, either a chemically treated or non-treated gene encoding a parent subtilase enzyme is subjected to PCR under conditions that increase the misincorporation of nucleotides (Deshler 1992; Leung et al., *Technique,* 1, 1989, pp. 11-15).

The DNA sequence to be mutagenized may conveniently be present in a genomic or cDNA library prepared from an organism expressing the parent subtilase. Alternatively, the DNA sequence may be present on a suitable vector such as a plasmid or a bacteriophage, which as such may be incubated with or otherwise exposed to the mutagenising agent. The DNA to be mutagenized may also be present in a host cell either by being integrated in the genome of said cell or by being present on a vector harbored in the cell. Finally, the DNA to be mutagenized may be in isolated form. It will be understood that the DNA sequence to be subjected to random mutagenesis is preferably a cDNA or a genomic DNA sequence.

In some cases it may be convenient to amplify the mutated DNA sequence prior to performing the expression step b) or the screening step c). Such amplification may be performed in accordance with methods known in the art, the presently preferred method being PCR-generated amplification using oligonucleotide primers prepared on the basis of the DNA or amino acid sequence of the parent enzyme.

The mutated DNA sequence may further comprise a DNA sequence encoding functions permitting expression of the mutated DNA sequence.

Localised Random Mutagenesis

The random mutagenesis may be advantageously localised to a part of the parent subtilase in question. This may, e.g., be advantageous when certain regions of the enzyme have been identified to be of particular importance for a given property of the enzyme, and when modified are expected to result in a variant having improved properties. Such regions may normally be identified when the tertiary structure of the parent enzyme has been elucidated and related to the function of the enzyme.

The localised or region-specific, random mutagenesis is conveniently performed by use of PCR generated mutagenesis techniques as described above or any other suitable technique known in the art. Alternatively, the DNA sequence encoding the part of the DNA sequence to be modified may be isolated, e.g., by insertion into a suitable vector, and said part may be subsequently subjected to mutagenesis by use of any of the mutagenesis methods discussed above.

General Method for Random Mutagenesis by Use of the DOPE Program

The random mutagenesis may be carried out by the following steps:

1. Select regions of interest for modification in the parent enzyme
2. Decide on mutation sites and non-mutated sites in the selected region
3. Decide on which kind of mutations should be carried out, e.g. with respect to the desired stability and/or performance of the variant to be constructed
4. Select structurally reasonable mutations
5. Adjust the residues selected by step 3 with regard to step 4.
6. Analyse by use of a suitable dope algorithm the nucleotide distribution.
7. If necessary, adjust the wanted residues to genetic code realism, e.g. taking into account constraints resulting from the genetic code, e.g. in order to avoid introduction of stop codons; the skilled person will be aware that some codon combinations cannot be used in practice and will need to be adapted
8. Make primers
9. Perform random mutagenesis by use of the primers
10. Select resulting subtilase variants by screening for the desired improved properties.

Suitable dope algorithms for use in step 6 are well known in the art. One such algorithm is described by Tomandl, D. et al., 1997, Journal of Computer-Aided Molecular Design 11:29-38. Another algorithm is DOPE (Jensen, L J, Andersen, K V, Svendsen, A, and Kretzschmar, T (1998) Nucleic Acids Research 26:697-702).

Expression Vectors

A recombinant expression vector comprising a nucleic acid sequence encoding a subtilase variant of the invention may be any vector that may conveniently be subjected to recombinant DNA procedures and which may bring about the expression of the nucleic acid sequence.

The choice of vector will often depend on the host cell into which it is to be introduced. Examples of a suitable vector include a linear or closed circular plasmid or a virus. The vector may be an autonomously replicating vector, i.e., a vector which exists as an extra-chromosomal entity, the replication of which is independent of chromosomal replication, e.g., a plasmid, an extra-chromosomal element, a mini chromosome, or an artificial chromosome. The vector may contain any means for assuring self-replication. Examples of bacterial origins of replication are the origins of replication of plasmids pBR322, pUC19, pACYC177, pACYC184, pUB110, pE194, pTA1060, and pAMR1. Examples of origin of replications for use in a yeast host cell are the 2 micron origin of replication, the combination of CEN6 and ARS4, and the combination of CEN3 and ARS1. The origin of replication may be one having a mutation which makes it function as temperature-sensitive in the host cell (see, e.g., Ehrlich, 1978, Proceedings of the National Academy of Sciences USA 75:1433).

Alternatively, the vector may be one which, when introduced into the host cell, is integrated into the genome and replicated together with the chromosome(s) into which it has been integrated. Vectors which are integrated into the genome of the host cell may contain any nucleic acid sequence enabling integration into the genome, in particular it may contain nucleic acid sequences facilitating integration into the genome by homologous or non-homologous recombination. The vector system may be a single vector, e.g. plasmid or virus, or two or more vectors, e.g. plasmids or virus', which together contain the total DNA to be introduced into the genome of the host cell, or a transposon.

The vector may in particular be an expression vector in which the DNA sequence encoding the subtilase variant of the invention is operably linked to additional segments or control sequences required for transcription of the DNA. The term, "operably linked" indicates that the segments are arranged so that they function in concert for their intended purposes, e.g. transcription initiates in a promoter and proceeds through the DNA sequence encoding the subtilase variant. Additional segments or control sequences include a promoter, a leader, a polyadenylation sequence, a propeptide sequence, a signal sequence and a transcription terminator. At a minimum the control sequences include a promoter and transcriptional and translational stop signals.

The promoter may be any DNA sequence that shows transcriptional activity in the host cell of choice and may be derived from genes encoding proteins either homologous or heterologous to the host cell.

Examples of suitable promoters for use in bacterial host cells include the promoter of the *Bacillus subtilis* levansucrase gene (sacB), the *Bacillus stearothermophilus* maltogenic amylase gene (amyM), the *Bacillus licheniformis* alpha-amylase gene (amyL), the *Bacillus amyloliquefaciens* alpha-amylase gene (amyQ), the *Bacillus subtilis* alkaline protease gene, or the *Bacillus pumilus* xylosidase gene, the *Bacillus amyloliquefaciens* BAN amylase gene, the *Bacillus licheniformis* penicillinase gene (penP), the *Bacillus subtilis* xylA and xylB genes, and the prokaryotic beta-lactamase gene (VIIIa-Kamaroff et al., 1978, Proceedings of the National Academy of Sciences USA 75:3727-3731). Other examples include the phage Lambda $P_R$ or $P_L$ promoters or the *E. coli* lac, trp or tac promoters or the *Streptomyces coelicolor* agarase gene (dagA). Further promoters are described in "Useful proteins from recombinant bacteria" in Scientific American, 1980, 242:74-94; and in Sambrook et al., 1989, supra.

Examples of suitable promoters for use in a filamentous fungal host cell are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium oxysporum* trypsin-like protease (as described in U.S. Pat. No. 4,288,627, which is incorporated herein by reference), and hybrids thereof. Particularly preferred promoters for use in filamentous fungal host cells are the TAKA amylase, NA2-tpi (a hybrid of the promoters from the genes encoding *Aspergillus niger* neutral (-amylase and *Aspergillus oryzae* triose phosphate isomerase), and glaA promoters. Further suitable promoters for use in filamentous fungus host cells are the ADH3 promoter (McKnight et al., The EMBO J. 4 (1985), 2093-2099) or the tpiA promoter.

Examples of suitable promoters for use in yeast host cells include promoters from yeast glycolytic genes (Hitzeman et al., J. Biol. Chem. 255 (1980), 12073-12080; Alber and Kawasaki, J. Mol. Appl. Gen. 1 (1982), 419-434) or alcohol dehydrogenase genes (Young et al., in Genetic Engineering of Microorganisms for Chemicals (Hollaender et al, eds.), Plenum Press, New York, 1982), or the TPI1 (U.S. Pat. No. 4,599,311) or ADH2-4-c (Russell et al., Nature 304 (1983), 652-654) promoters.

Further useful promoters are obtained from the *Saccharomyces cerevisiae* enolase (ENO-1) gene, the *Saccharomyces cerevisiae* galactokinase gene (GAL1), the *Saccharomyces cerevisiae* alcohol dehydrogenase/glyceraldehyde-3-phosphate dehydrogenase genes (ADH2/GAP), and the *Saccharomyces cerevisiae* 3-phosphoglycerate kinase gene. Other useful promoters for yeast host cells are described by Romanos et al., 1992, Yeast 8:423-488. In a mammalian host cell, useful promoters include viral promoters such as those from Simian Virus 40 (SV40), Rous sarcoma virus (RSV), adenovirus, and bovine papilloma virus (BPV).

Examples of suitable promoters for use in mammalian cells are the SV40 promoter (Subramani et al., Mol. Cell. Biol. 1 (1981), 854-864), the MT-1 (metallothionein gene) promoter (Palmiter et al., Science 222 (1983), 809-814) or the adenovirus 2 major late promoter.

An example of a suitable promoter for use in insect cells is the polyhedrin promoter (U.S. Pat. No. 4,745,051; Vasuvedan et al., FEBS Lett. 311, (1992) 7-11), the P10 promoter (J. M. Vlak et al., J. Gen. Virology 69, 1988, pp. 765-776), the *Autographa californica* polyhedrosis virus basic protein promoter (EP 397 485), the baculovirus immediate early gene 1 promoter (U.S. Pat. No. 5,155,037; U.S. Pat. No. 5,162,222), or the baculovirus 39K delayed-early gene promoter (U.S. Pat. No. 5,155,037; U.S. Pat. No. 5,162,222).

The DNA sequence encoding a subtilase variant of the invention may also, if necessary, be operably connected to a suitable terminator.

The recombinant vector of the invention may further comprise a DNA sequence enabling the vector to replicate in the host cell in question.

The vector may also comprise a selectable marker, e.g. a gene the product of which complements a defect in the host cell, or a gene encoding resistance to e.g. antibiotics like ampicillin, kanamycin, chloramphenicol, erythromycin, tetracycline, spectinomycine, neomycin, hygromycin, methotrexate, or resistance to heavy metals, virus or herbicides, or which provides for prototrophy or auxotrophs. Examples of bacterial selectable markers are the dal genes from *Bacillus subtilis* or *Bacillus licheniformis*, resistance. A frequently used mammalian marker is the dihydrofolate reductase gene (DHFR). Suitable markers for yeast host cells are ADE2, HIS3, LEU2, LYS2, MET3, TRP1, and URA3. A selectable marker for use in a filamentous fungal host cell may be selected from the group including, but not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), and glufosinate resistance markers, as well as equivalents from other species. Particularly, for use in an *Aspergillus* cell are the amdS and pyrG markers of *Aspergillus nidulans* or *Aspergillus oryzae* and the bar marker of *Streptomyces hygroscopicus*. Furthermore, selection may be accomplished by co-transformation, e.g., as described in WO 91/17243, where the selectable marker is on a separate vector.

To direct a subtilase variant of the present invention into the secretory pathway of the host cells, a secretory signal sequence (also known as a leader sequence, prepro sequence or pre sequence) may be provided in the recombinant vector. The secretory signal sequence is joined to the DNA sequence encoding the enzyme in the correct reading frame. Secretory signal sequences are commonly positioned 5' to the DNA sequence encoding the enzyme. The secretory signal sequence may be that normally associated with the enzyme or may be from a gene encoding another secreted protein.

The procedures used to ligate the DNA sequences coding for the present enzyme, the promoter and optionally the terminator and/or secretory signal sequence, respectively, or to assemble these sequences by suitable PCR amplification schemes, and to insert them into suitable vectors containing the information necessary for replication or integration, are well known to persons skilled in the art (cf., for instance, Sambrook et al.).

More than one copy of a nucleic acid sequence encoding an enzyme of the present invention may be inserted into the host cell to amplify expression of the nucleic acid sequence. Stable amplification of the nucleic acid sequence can be obtained by integrating at least one additional copy of the sequence into the host cell genome using methods well known in the art and selecting for transformants.

The nucleic acid constructs of the present invention may also comprise one or more nucleic acid sequences which encode one or more factors that are advantageous in the expression of the polypeptide, e.g., an activator (e.g., a trans-acting factor), a chaperone, and a processing protease. Any factor that is functional in the host cell of choice may be used in the present invention. The nucleic acids encoding one or more of these factors are not necessarily in tandem with the nucleic acid sequence encoding the polypeptide.

Host Cells

The DNA sequence encoding a subtilase variant of the present invention may be either homologous or heterologous to the host cell into which it is introduced. If homologous to the host cell, i.e. produced by the host cell in nature, it will typically be operably connected to another promoter sequence or, if applicable, another secretory signal sequence and/or terminator sequence than in its natural environment. The term "homologous" is intended to include a DNA sequence encoding an enzyme native to the host organism in question. The term "heterologous" is intended to include a DNA sequence not expressed by the host cell in nature. Thus, the DNA sequence may be from another organism, or it may be a synthetic sequence.

The host cell into which the DNA construct or the recombinant vector of the invention is introduced may be any cell that is capable of producing the present subtilase variants, such as prokaryotes, e.g. bacteria or eukaryotes, such as fungal cells, e.g. yeasts or filamentous fungi, insect cells, plant cells or mammalian cells.

Examples of bacterial host cells which, on cultivation, are capable of producing the subtilase variants of the invention are gram-positive bacteria such as strains of *Bacillus*, e.g. strains of *B. subtilis, B. licheniformis, B. lentus, B. brevis, B. stearothermophilus, B. alkalophilus, B. amyloliquefaciens, B. coagulans, B. circulans, B. lautus, B. megaterium* or *B. thuringiensis*, or strains of *Streptomyces*, such as *S. lividans* or *S. murinus*, or gram-negative bacteria such as *Escherichia coli* or *Pseudomonas* sp.

The transformation of the bacteria may be effected by protoplast transformation, electroporation, conjugation, or by using competent cells in a manner known per se (cf. Sambrook et al., supra).

When expressing the subtilase variant in bacteria such as *E. coli*, the enzyme may be retained in the cytoplasm, typically as insoluble granules (known as inclusion bodies), or it may be directed to the periplasmic space by a bacterial secretion sequence. In the former case, the cells are lysed and the granules are recovered and denatured after which the enzyme is refolded by diluting the denaturing agent. In the latter case, the enzyme may be recovered from the periplasmic space by disrupting the cells, e.g. by sonication or osmotic shock, to release the contents of the periplasmic space and recovering the enzyme.

When expressing the subtilase variant in gram-positive bacteria such as *Bacillus* or *Streptomyces* strains, the enzyme may be retained in the cytoplasm, or it may be directed to the extracellular medium by a bacterial secretion sequence. In the latter case, the enzyme may be recovered from the medium as described below.

Examples of host yeast cells include cells of a species of *Candida, Kluyveromyces, Saccharomyces, Schizosaccharomyces, Pichia, Hansehula*, or *Yarrowia*. In a particular embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. Other useful yeast host cells are a *Kluyveromyces lactis, Kluyveromyces fragilis, Hansehula polymorpha, Pichia pastoris, Yarrowia lipolytica, Schizosaccharomyces pombe, Ustilgo maylis, Candida maltose, Pichia guillermondii* and *Pichia methanolio* cell (cf. Gleeson et al., J. Gen. Microbiol. 132, 1986, pp. 3459-3465; U.S. Pat. No. 4,882,279 and U.S. Pat. No. 4,879,231). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium Series No. 9, 1980. The biology of yeast and manipulation of yeast genetics are well known in the art (see, e.g., Biochemistry and Genetics of Yeast, Bacil, M., Horecker, B. J., and Stopani, A. O. M., editors, 2nd edition, 1987; The Yeasts, Rose, A. H., and Harrison, J. S., editors, 2nd edition, 1987; and The Molecular Biology of the Yeast *Saccharomyces*, Strathern et al., editors, 1981). Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, Journal of Bacteriology 153:163; and Hinnen et al., 1978, Proceedings of the National Academy of Sciences USA 75:1920.

Examples of filamentous fungal cells include filamentous forms of the subdivision Eumycota and Oomycota (as defined by Hawksworth et al., 1995, supra), in particular it may of the a cell of a species of *Acremonium*, such as *A. chrysogenum*, *Aspergillus*, such as *A. awamori, A. foetidus, A. japonicus, A. niger, A. nidulans* or *A. oryzae*, *Fusarium*, such as *F. bactridioides, F. cerealis, F. crookwellense, F. culmorum, F. graminearum, F. graminum, F. heterosporum, F. negundi, F. reticulatum, F. roseum, F. sambucinum, F. sarcochroum, F. sulphureum, F. trichothecioides* or *F. oxysporum, Humicola*, such as *H. insolens* or *H. lanuginose, Mucor*, such as *M. miehei, Myceliophthora*, such as *M. thermophilum, Neurospora*, such as *N. crassa, Penicillium*, such as *P. purpurogenum, Thielavia*, such as *T. terrestris, Tolypocladium*, or *Trichoderma*, such as *T. harzianum, T. koningii, T. longibrachiatum, T. reesei* or *T. viride*, or a teleomorph or synonym thereof. The use of *Aspergillus* spp. for the expression of proteins is described in, e.g., EP 272 277, EP 230 023.

Examples of insect cells include a *Lepidoptera* cell line, such as *Spodoptera frugiperda* cells or *Trichoplusia ni* cells (cf. U.S. Pat. No. 5,077,214). Culture conditions may suitably be as described in WO 89/01029 or WO 89/01028. Transformation of insect cells and production of heterologous polypeptides therein may be performed as described in U.S. Pat. No. 4,745,051; 4,775,624; 4,879,236; 5,155,037; 5,162,222; EP 397,485).

Examples of mammalian cells include Chinese hamster ovary (CHO) cells, HeLa cells, baby hamster kidney (BHK) cells, COS cells, or any number of other immortalized cell lines available, e.g., from the American Type Culture Collection. Methods of transfecting mammalian cells and expressing DNA sequences introduced in the cells are described in e.g. Kaufman and Sharp, J. Mol. Biol. 159 (1982), 601-621; Southern and Berg, J. Mol. Appl. Genet. 1 (1982), 327-341; Loyter et al., Proc. Natl. Acad. Sci. USA 79 (1982), 422-426; Wigler et al., Cell 14 (1978), 725; Corsaro and Pearson, Somatic Cell Genetics 7 (1981), 603, Ausubel et al., Current Protocols in Molecular Biology, John Wiley and Sons, Inc., N.Y., 1987, Hawley-Nelson et al., Focus 15 (1993), 73; Ciccarone et al., Focus 15 (1993), 80; Graham and van der Eb, Virology 52 (1973), 456; and Neumann et al., EMBO J. 1 (1982), 841-845. Mammalian cells may be transfected by direct uptake using the calcium phosphate precipitation method of Graham and Van der Eb (1978, Virology 52:546).

Methods for Expression and Isolation of Proteins

To express an enzyme of the present invention the above mentioned host cells transformed or transfected with a vector comprising a nucleic acid sequence encoding an enzyme of the present invention are typically cultured in a suitable nutrient medium under conditions permitting the production of the desired molecules, after which these are recovered from the cells, or the culture broth.

The medium used to culture the host cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The media may be prepared using procedures known in the art (see, e.g., references for bacteria and yeast; Bennett, J. W. and LaSure, L., editors, More Gene Manipulations in Fungi, Academic Press, CA, 1991).

If the enzymes of the present invention are secreted into the nutrient medium, they may be recovered directly from the medium. If they are not secreted, they may be recovered from cell lysates. The enzymes of the present invention may be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gelfiltration chromatography, affinity chromatography, or the like, dependent on the enzyme in question.

The enzymes of the invention may be detected using methods known in the art that are specific for these proteins. These detection methods include use of specific antibodies, formation of a product, or disappearance of a substrate. For example, an enzyme assay may be used to determine the activity of the molecule. Procedures for determining various kinds of activity are known in the art.

The enzymes of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., Protein Purification, J-C Janson and Lars Ryden, editors, VCH Publishers, New York, 1989).

When an expression vector comprising a DNA sequence encoding an enzyme of the present invention is transformed/transfected into a heterologous host cell it is possible to enable heterologous recombinant production of the enzyme. An advantage of using a heterologous host cell is that it is possible to make a highly purified enzyme composition, characterized in being free from homologous impurities, which are often present when a protein or peptide is expressed in a homologous host cell. In this context homologous impurities mean any impurity (e.g. other polypeptides than the enzyme of the invention) which originates from the homologous cell where the enzyme of the invention is originally obtained from.

Detergent Applications

The enzyme of the invention may be added to and thus become a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations, especially for automatic dish washing (ADW).

In a specific aspect, the invention provides a detergent additive comprising the enzyme of the invention. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Preferred commercially available protease enzymes include Alcalase™, Savinase™, Primase™, Duralase™, Esperase™, and Kannase™ (Novozymes A/S), Maxatase™, Maxacal™, Maxapem™, Properase™, Purafect™, Purafect OxP™, FN2™, and FN3™ (Genencor International Inc.).

Lipases: Suitable lipases include those of bacterial or fungal origin. Chemically modified or protein engineered mutants are included. Examples of useful lipases include lipases from *Humicola* (synonym *Thermomyces*), e.g. from *H. lanuginosa* (*T. lanuginosus*) as described in EP 258 068 and EP 305 216 or from *H. insolens* as described in WO 96/13580, a *Pseudomonas* lipase, e.g. from *P. alcaligenes* or *P. pseudoalcaligenes* (EP 218 272), *P. cepacia* (EP 331 376), *P. stutzeri* (GB 1,372,034), *P. fluorescens*, *Pseudomonas* sp. strain SD 705 (WO 95/06720 and WO 96/27002), *P. wisconsinensis* (WO 96/12012), a *Bacillus* lipase, e.g. from *B. subtilis* (Dartois et al. (1993), Biochemica et Biophysica Acta, 1131, 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipolase™ and Lipolase Ultra™ (Novozymes A/S).

Amylases: Suitable amylases (α and/or β) include those of bacterial or fungal origin. Chemically modified or protein engineered mutants are included. Amylases include, for example, α-amylases obtained from *Bacillus*, e.g. a special strain of *B. licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, Fungamyl™ and BAN™ (Novozymes A/S), Rapidase™ and Purastar™ (from Genencor International Inc.).

Cellulases: Suitable cellulases include those of bacterial or fungal origin. Chemically modified or protein engineered mutants are included. Suitable cellulases include cellulases from the genera *Bacillus*, *Pseudomonas*, *Humicola*, *Fusarium*, *Thielavia*, *Acremonium*, e.g. the fungal cellulases produced from *Humicola insolens*, *Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and PCT/DK98/00299.

Commercially available cellulases include Celluzyme™, and Carezyme™ (Novozymes A/S), Clazinase™, and Puradax HA™ (Genencor International Inc.), and KAC-500 (B)™ (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g. from *C. cinereus*, and variants thereof as those described in WO 93/24618, WO 95/10602, and WO 98/15257.

Commercially available peroxidases include Guardzyme™ (Novozymes A/S).

The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated e.g. as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinylpyrrolidone), poly (ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

In the detergent compositions any enzyme, in particular the enzyme of the invention, may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

The enzyme of the invention may additionally be incorporated in the detergent formulations disclosed in WO 97/07202 which is hereby incorporated as reference.

Materials and Methods
Textiles
Standard textile pieces are obtained from EMPA St. Gallen, Lerchfeldstrasse 5, CH-9014 St. Gallen, Switzerland. Especially type EMPA 116 (cotton textile stained with blood, milk and ink) and EMPA 117 (polyester/cotton textile stained with blood, milk and ink). Other atandard textile pieces are obtained from wfk-Cleaning Technology Research Institute, Christenfeld 10, D-41379 Brüggen-Bracht, Germany. Especially type wfk10N (cotton textile stained with egg/pigment), wfk10eggEG (cotton textile stained with egg yolk). Denaturation of wfk10N occurs in an autoclave.

Method for Producing a Subtilase Variant

The present invention provides a method of producing an isolated enzyme according to the invention, wherein a suitable host cell, which has been transformed with a DNA sequence encoding the enzyme, is cultured under conditions permitting the production of the enzyme, and the resulting enzyme is recovered from the culture.

When an expression vector comprising a DNA sequence encoding the enzyme is transformed into a heterologous host cell it is possible to enable heterologous recombinant production of the enzyme of the invention. Thereby it is possible to make a highly purified subtilase composition, characterized in being free from homologous impurities.

The medium used to culture the transformed host cells may be any conventional medium suitable for growing the host cells in question. The expressed subtilase may conveniently be secreted into the culture medium and may be recovered there-from by well-known procedures including separating the cells from the medium by centrifugation or filtra-tion, precipitating proteinaceous components of the medium by means of a salt such as ammonium sulfate, followed by chromatographic procedures such as ion exchange chromatography, affinity chromatography, or the like.

EXAMPLE 1

Removal of Ion-binding Sites from BPN' Like Subtilases

The below mentioned regions in JP170 and TY145 have been selected for transfer from JP170 and TY145 to Savinase. By use of the molecular methods of preparing subtilase variants as described herein, the Savinase regions (BPN' numbering) are deleted and the JP170 and TY145 regions are inserted instead. Since the Savinase regions are in contact with ion-binding sites, the purpose of the modifications is to remove the ion-binding site from Savinase.

| Savinase | region A194-L196 (SEQ ID NO: 8) |
|---|---|
| JP170 | region P209-P217 (SEQ ID NO: 1) and |
| Savinase | region L75-L82 (SEQ ID NO: 8) |
| TY145 | region H83-Y92 (SEQ ID NO: 7), | alternatively the modification can be

| Savinase | region A194-L196 (SEQ ID NO: 8) |
|---|---|
| JP170 | region P209-P217 (SEQ ID NO: 1) and |
| Savinase | region L75-L82 (SEQ ID NO: 8) |
| JP170 | region N79-K83 (SEQ ID NO: 1). |

Construction and Expression of Enzyme Variants:
Site-directed Mutagenesis:

Subtilase JP170 site-directed variants of the invention comprising specific insertions/deletions/substitutions are made by traditional cloning of DNA fragments (Sambrook et al., Molecular Cloning: A Laboratory Manual, 2nd Ed., Cold Spring Harbor, 1989) produced by PCR with oligos containing the desired mutations.

The template plasmid DNA may be pSX222, or an analogue of this containing a variant of subtilisin JP170. Mutations are introduced by oligo directed mutagenesis to the construction of variants.

The subtilisin JP170 variants were transformed into E. coli. DNA purified from an over night culture of these transformants is transformed into B. subtilis by restriction endonuclease digestion, purification of DNA fragments, ligation, transformation of B. subtilis. Transformation of B. subtilis is performed as described by Dubnau et al., 1971, J. Mol. Biol. 56, pp. 209-221.

Site-directed Mutgenesis in Order to Introduce Mutations in a Specific Region:

The overall strategy used to perform site-directed mutagenesis is:

Mutagenic primers (oligonucleotides) are synthesized corresponding to the DNA sequence flanking the sites of mutation, separated by the DNA base pairs defining the insertions/deletions/substitutions.

Subsequently, the resulting mutagenic primers are used in a PCR reaction with the modified plasmid pSX222. The resulting PCR fragment is purified and extended in a second PCR-reaction, the resulting PCR product is purified and extended in a third PCR-reaction before being digested by endonucleases and cloned into the *E. coli-B. subtilis* shuttle vector pSX222. The PCR reactions are performed under normal conditions. The plasmid DNA is transformed into *E. coli* by well-known techniques and one *E. coli* colony is sequenced to confirm the mutation designed.

In order to purify subtilase variants of the invention, the pSX222 expression plasmid comprising a variant of the invention was transformed into a competent *B. subtilis* strain and fermented as described above.

EXAMPLE 2

Purification and Assessment of Enzyme Concentration

After fermentation, purification of subtilisin variants is accomplished using Hydrophobic Charge Induction Chromatography (HClC) and subsequent vacuum filtration. To capture the enzyme, the HClC uses a cellulose matrix to which 4-Mercapto-Ethyl-Pyridine (4-MEP) is bound.

Beads of the cellulose matrix sized 80-100 µm are mixed with a media containing yeast and the transformed *B. subtilis* capable of secreting the subtilisin variants and incubated at pH 9.5 in Unifilter® microplates.

As 4-MEP is hydrophobic at pH>7 and the subtilisin variants are hydrophobic at pH 9.5 a hydrophobic association is made between the secreted enzyme and the 4-MEP on the beads. After incubation the media and cell debris is removed by vacuum filtration while the beads and enzyme are kept on the filter.

To elute the enzyme from the beads the pH is now lowered by washing the filter with an elution buffer (pH 5). Hereby the enzymes part from the beads and can be retrieved from the buffer.

The concentration of the purified subtilisin enzyme variants is assessed by active site titration (AST).

The purified enzyme is incubated with the high affinity inhibitor Cl-2A at different concentrations to inhibit a varying amount of the active sites. The protease and inhibitor binds to each other at a 1:1 ratio and accordingly the enzyme concentration can be directly related to the concentration of inhibitor, at which all protease is inactive. To measure the residual protease activity, a substrate (0.6 mM Suc-Ala-Ala-Pro-Phe-pNA in Tris/HCl buffer) is added after the incubation with inhibitor and during the following 4 minutes the development of the degradation product pNA (paranitrophenol) is measured periodically at 405 nm on an Elisa Reader.

Each of the variants listed below were constructed as described above. H243K; S238K; L233T; L233S; L233D; Y247R; H200D; H200A; H200G; E185D; S193Q; S193Y; N390D; G394N; G394F; W240H; G355A; G355S; N316D; N79D; K246R; K83R; H200D+D196N; H243E.

EXAMPLE 3

Automatic Mechanical Stress Assay (AMSA)

Description of AMSA-test Method:

Washing experiments are performed in order to assess the wash performance of selected JP170 subtilase variants in detergent compositions. Subtilases of the present application were tested using the Automatic Mechanical Stress Assay (AMSA). With the AMSA, the wash performance of a large quantity of small volume enzyme-detergent solutions can be examined. The AMSA plate has a number of slots for test solutions and a lid firmly squeezing the textile swatch to be washed against all the slot openings. During the washing time, the plate, test solutions, textile and lid are vigorously shaken to bring the test solution in contact with the textile and apply mechanical stress in a regular, periodic oscillating manner. For further description see WO 02/42740 especially the paragraph "Special method embodiments" at page 23-24.

The experiment was conducted under the experimental conditions specified below:

| | |
|---|---|
| Commercial detergent base | European 3 in 1 ADW type |
| Detergent dosage | 5-5.5 g/L |
| Test solution volume | 160 µL |
| pH | As is |
| Wash time | 20 minutes |
| Temperature | 50° C. |
| Water hardness | 25° dH |
| Enzyme concentration in test solution | 0.25 mg/L, 0.5 mg/L, 1 mg/L, and 2.,5 mg/L for wfk10N; 1 mg/L, 2.5 mg/L, 4 mg/L, and 6 mg/L for denatured wfk10N. |
| Test material | Wfk10N |

Water hardness was adjusted to 9° dH by addition of $CaCl_2$, $MgCl_2$, and $NaHCO_3$ ($Ca^{2+}$: $Mg^{2+}$= 4:1) to the test system. After washing the textile pieces were glushed in tap water and dried.

The performance of the enzyme variant is measured as the brightness of the colour of the textile samples washed with that specific protease. Brightness can also be expressed as the intensity of the light reflected from the textile sample when illuminated with white light. When the textile is stained the intensity of the reflected light is lower, than that of a clean textile. Therefore the intensity of the reflected light can be used to measure wash performance of a shuffled protease.

Colour measurements are made with a professional flatbed scanner (PFU DL2400pro, obtainable from: J. M. Thomsen, Dorfgade 2, Dorf, Dronninglund, DK-9330), which is used to capture an image of the washed textile samples. The scans are made with a resolution of 200 dpi and with an output colour dept of 24 bits. In order to get accurate results, the scanner is frequently calibrated with a Kodak reflective IT8 target.

To extract a value for the light intensity from the scanned images, a special designed software application is used (Novozymes Color VectorAnalyzer). The program retrieves the 24 bit pixel values from the image and converts them into values for red, green and blue (RGB). The intensity value (Int) is calculated by adding the RGB values together as vectors and then taking the length of the resulting vector:

$$Int = \sqrt{r^2 + g^2 + b^2}.$$

Detergents

Detergents for wash performance tests of the subtilases of the invention can be obtained by purchasing fully formulated commercial detergents at the market and subsequently inactivate the enzymatic components by heat treatment (5 minutes at 85° C. in aqueous solution). Moreover a commercial detergent base without enzymes can be purchased directly from the manufacturer. Further a suitable model detergent can be purchased and used for wash performance tests.

The proteases may also be tested in a model detergent composition comprising

| | |
|---|---|
| Sodium Tripolyphosphate | 23.0% |
| Sodium Citrate Dihydrate | 22.3% |
| Sodium Perborate Monohydrate | 6.0% |
| Tetraacetyl Ethylendiamine | 2.0% |
| Sodium Disilicate (noncrystaline) | 5.0% |
| Linear Fatty Alcohol Ethoxylate (non-ionic surfactant, low foaming) | 2.0% |
| Maleic acid/Acrylic acid copolymer (Sodium salt, 50% active on Sodium Carbonate) | 4.0% |
| Sodium Carbonate, anhydrous add to | 100% |

Using the above test method in combination with a commercially available detergent the results shown below were obtained. As it appears, the subtilases according to the invention exhibits improved wash performance on egg stains in comparison to the wild type JP170 subtilase with SEQ ID NO:1.

| Mutations WT JP170 | AMSA REF | "peptide binding loop" |
|---|---|---|
| S193Q (SEQ ID NO: 1) | ≧ | S193Y (Ca-site 1) |
| S193Y (SEQ ID NO: 1) | ≧ | N390D (Ca-site 2) |
| N390D (SEQ ID NO: 1) | ≧ | G394N (Ca-site 3) |
| G394N (SEQ ID NO: 1) | > | G394F (Ca-site 3) |
| G394F (SEQ ID NO: 1) | ≧ | W240H (temperature stability) |
| W240H (SEQ ID NO: 1) | ≧ | G355A (temperature stability) |
| G355A (SEQ ID NO: 1) | ≧ | G355S (temperature stability) |
| K246R (SEQ ID NO: 1) | ≧ | K83R (surface charge distribution) |
| H200D + D196N (SEQ ID NO: 1) | ≧ | (Ca-site 1) |

The invention claimed is:

1. A variant of a JP170 type subtilase, said variant having at least 70% identity to SEQ ID NO:1 and comprising one or more disulfide bridges introduced by one or more of the following modifications: A4C+P222C, G21C+A86C, V26C+A265C, G57C+G105C, G74C+A229C, Q111C+N143C, G160C+S170C, A286C+V349C, A27C+A122C, A45C+G78C, V72C+P258C, G78C+A229C, D98C+G104C, Q111C+Y147C, G135C+G167C, R142C+P354C, V144C+A178C, G182C+P217C, A183C+G223C, A195C+Y225C, F271C+P279C, A287C+A430C, A293C+T310C, E322C+S428C, S324C+A332C, S327C+P424C, D352C+N397C, G355C+T362C, G291C+S314C, wherein the positions correspond to the positions of the amino acid sequence set forth in SEQ ID NO:1, and wherein the variant subtilase hydrolyzes Suc-Ala-Ala-Pro-Phe-paranitroanilide.

2. The JP170 type subtilase variant of claim 1 comprising one or more of the modifications: A4C+P222C, G21C+A86C, V26C+A265C, A27C+A117C, G57C+G105C, G74C+A229C, Q111C+Y143C, G160C+S170C, A286C+V349C.

3. The JP170 type subtilase variant of claim 1 having at least 80% identity to SEQ ID NO: 1.

4. The JP170 type subtilase variant of claim 1 having at least 85% identity to SEQ ID NO: 1.

5. The JP170 type subtilase variant of claim 1 having at least 90% identity to SEQ ID NO: 1.

6. The JP170 type subtilase variant of claim 1 having at least 91% identity to SEQ ID NO: 1.

7. The JP170 type subtilase variant of claim 1 having at least 92% identity to SEQ ID NO: 1.

8. The JP170 type subtilase variant of claim 1 having at least 93% identity to SEQ ID NO: 1.

9. The JP170 type subtilase variant of claim 1 having at least 94% identity to SEQ ID NO: 1.

10. The JP170 type subtilase variant of claim 1 having at least 95% identity to SEQ ID NO: 1.

11. The JP170 type subtilase variant of claim 1 having at least 96% identity to SEQ ID NO: 1.

12. The JP170 type subtilase variant of claim 1 having at least 97% identity to SEQ ID NO: 1.

13. The JP170 type subtilase variant of claim 1 having at least 98% identity to SEQ ID NO: 1.

14. The JP170 type subtilase variant of claim 1 having at least 99% identity to SEQ ID NO: 1.

15. A detergent composition comprising the JP170 type subtilase variant of claim 1 and a surfactant.

* * * * *

```
                        SEQUENCE LISTING

<160> NUMBER OF SEQ ID NOS: 8

<210> SEQ ID NO 1
<211> LENGTH: 433
<212> TYPE: PRT
<213> ORGANISM: Bacillus species JP170

<400> SEQUENCE: 1

Asn Asp Val Ala Arg Gly Ile Val Lys Ala Asp Val Ala Gln Asn Asn
1               5                   10                  15

Phe Gly Leu Tyr Gly Gln Gly Gln Ile Val Ala Val Ala Asp Thr Gly
            20                  25                  30

Leu Asp Thr Gly Arg Asn Asp Ser Ser Met His Glu Ala Phe Arg Gly
        35                  40                  45

Lys Ile Thr Ala Leu Tyr Ala Leu Gly Arg Thr Asn Asn Ala Asn Asp
50                  55                  60

Pro Asn Gly His Gly Thr His Val Ala Gly Ser Val Leu Gly Asn Ala
65                  70                  75                  80

Thr Asn Lys Gly Met Ala Pro Gln Ala Asn Leu Val Phe Gln Ser Ile
                85                  90                  95

Met Asp Ser Gly Gly Leu Gly Gly Leu Pro Ala Asn Leu Gln Thr
            100                 105                 110

Leu Phe Ser Gln Ala Tyr Ser Ala Gly Ala Arg Ile His Thr Asn Ser
        115                 120                 125

Trp Gly Ala Pro Val Asn Gly Ala Tyr Thr Thr Asp Ser Arg Asn Val
    130                 135                 140

Asp Asp Tyr Val Arg Lys Asn Asp Met Thr Ile Leu Phe Ala Ala Gly
145                 150                 155                 160

Asn Glu Gly Pro Gly Ser Gly Thr Ile Ser Ala Pro Gly Thr Ala Lys
                165                 170                 175

Asn Ala Ile Thr Val Gly Ala Thr Glu Asn Leu Arg Pro Ser Phe Gly
            180                 185                 190

Ser Tyr Ala Asp Asn Ile Asn His Val Ala Gln Phe Ser Ser Arg Gly
        195                 200                 205

Pro Thr Arg Asp Gly Arg Ile Lys Pro Asp Val Met Ala Pro Gly Thr
    210                 215                 220
```

```
Tyr Ile Leu Ser Ala Arg Ser Ser Leu Ala Pro Asp Ser Ser Phe Trp
225                 230                 235                 240

Ala Asn His Asp Ser Lys Tyr Ala Tyr Met Gly Gly Thr Ser Met Ala
                245                 250                 255

Thr Pro Ile Val Ala Gly Asn Val Ala Gln Leu Arg Glu His Phe Val
            260                 265                 270

Lys Asn Arg Gly Val Thr Pro Lys Pro Ser Leu Leu Lys Ala Ala Leu
        275                 280                 285

Ile Ala Gly Ala Asp Val Gly Leu Gly Phe Pro Asn Gly Asn Gln
290                 295                 300

Gly Trp Gly Arg Val Thr Leu Asp Lys Ser Leu Asn Val Ala Phe Val
305                 310                 315                 320

Asn Glu Thr Ser Pro Leu Ser Thr Ser Gln Lys Ala Thr Tyr Ser Phe
                325                 330                 335

Thr Ala Gln Ala Gly Lys Pro Leu Lys Ile Ser Leu Val Trp Ser Asp
            340                 345                 350

Ala Pro Gly Ser Thr Thr Ala Ser Leu Thr Leu Val Asn Asp Leu Asp
        355                 360                 365

Leu Val Ile Thr Ala Pro Asn Gly Thr Lys Tyr Val Gly Asn Asp Phe
370                 375                 380

Thr Ala Pro Tyr Asp Asn Asn Trp Asp Gly Arg Asn Asn Val Glu Asn
385                 390                 395                 400

Val Phe Ile Asn Ala Pro Gln Ser Gly Thr Tyr Thr Val Glu Val Gln
                405                 410                 415

Ala Tyr Asn Val Pro Val Ser Pro Gln Thr Phe Ser Leu Ala Ile Val
            420                 425                 430

His

<210> SEQ ID NO 2
<211> LENGTH: 433
<212> TYPE: PRT
<213> ORGANISM: Bacillus species Y

<400> SEQUENCE: 2

Asn Asp Val Ala Arg Gly Ile Val Lys Ala Asp Val Ala Gln Asn Asn
1               5                   10                  15

Tyr Gly Leu Tyr Gly Gln Gly Gln Leu Val Ala Val Ala Asp Thr Gly
                20                  25                  30

Leu Asp Thr Gly Arg Asn Asp Ser Ser Met His Glu Ala Phe Arg Gly
            35                  40                  45

Lys Ile Thr Ala Leu Tyr Ala Leu Gly Arg Thr Asn Asn Ala Ser Asp
50                  55                  60

Pro Asn Gly His Gly Thr His Val Ala Gly Ser Val Leu Gly Asn Ala
65                  70                  75                  80

Leu Asn Lys Gly Met Ala Pro Gln Ala Asn Leu Val Phe Gln Ser Ile
                85                  90                  95

Met Asp Ser Ser Gly Gly Leu Gly Gly Leu Pro Ser Asn Leu Asn Thr
            100                 105                 110

Leu Phe Ser Gln Ala Trp Asn Ala Gly Ala Arg Ile His Thr Asn Ser
        115                 120                 125

Trp Gly Ala Pro Val Asn Gly Ala Tyr Thr Ala Asn Ser Arg Gln Val
    130                 135                 140

Asp Glu Tyr Val Arg Asn Asn Asp Met Thr Val Leu Phe Ala Ala Gly
145                 150                 155                 160

Asn Glu Gly Pro Asn Ser Gly Thr Ile Ser Ala Pro Gly Thr Ala Lys
```

```
                    165                 170                 175
Asn Ala Ile Thr Val Gly Ala Thr Glu Asn Tyr Arg Pro Ser Phe Gly
                180                 185                 190

Ser Ile Ala Asp Asn Pro Asn His Ile Ala Gln Phe Ser Ser Arg Gly
            195                 200                 205

Ala Thr Arg Asp Gly Arg Ile Lys Pro Asp Val Thr Ala Pro Gly Thr
        210                 215                 220

Phe Ile Leu Ser Ala Arg Ser Ser Leu Ala Pro Asp Ser Ser Phe Trp
225                 230                 235                 240

Ala Asn Tyr Asn Ser Lys Tyr Ala Tyr Met Gly Gly Thr Ser Met Ala
                245                 250                 255

Thr Pro Ile Val Ala Gly Asn Val Ala Gln Leu Arg Glu His Phe Ile
                260                 265                 270

Lys Asn Arg Gly Ile Thr Pro Lys Pro Ser Leu Ile Lys Ala Ala Leu
            275                 280                 285

Ile Ala Gly Ala Thr Asp Val Gly Leu Gly Tyr Pro Ser Gly Asp Gln
        290                 295                 300

Gly Trp Gly Arg Val Thr Leu Asp Lys Ser Leu Asn Val Ala Tyr Val
305                 310                 315                 320

Asn Glu Ala Thr Ala Leu Ala Thr Gly Gln Lys Ala Thr Tyr Ser Phe
                325                 330                 335

Gln Ala Gln Ala Gly Lys Pro Leu Lys Ile Ser Leu Val Trp Thr Asp
                340                 345                 350

Ala Pro Gly Ser Thr Thr Ala Ser Tyr Thr Leu Val Asn Asp Leu Asp
            355                 360                 365

Leu Val Ile Thr Ala Pro Asn Gly Gln Lys Tyr Val Gly Asn Asp Phe
        370                 375                 380

Ser Tyr Pro Tyr Asp Asn Asn Trp Asp Gly Arg Asn Asn Val Glu Asn
385                 390                 395                 400

Val Phe Ile Asn Ala Pro Gln Ser Gly Thr Tyr Ile Ile Glu Val Gln
                405                 410                 415

Ala Tyr Asn Val Pro Ser Gly Pro Gln Arg Phe Ser Leu Ala Ile Val
                420                 425                 430

His

<210> SEQ ID NO 3
<211> LENGTH: 433
<212> TYPE: PRT
<213> ORGANISM: Bacillus species SD-521

<400> SEQUENCE: 3

Asn Asp Val Ala Arg Gly Ile Val Lys Ala Asp Val Ala Gln Asn Asn
1               5                   10                  15

Tyr Gly Leu Tyr Gly Gln Gly Gln Val Val Ala Val Ala Asp Thr Gly
                20                  25                  30

Leu Asp Thr Gly Arg Asn Asp Ser Ser Met His Glu Ala Phe Arg Gly
            35                  40                  45

Lys Ile Thr Ala Leu Tyr Ala Leu Gly Arg Thr Asn Asn Ala Asn Asp
        50                  55                  60

Pro Asn Gly His Gly Thr His Val Ala Gly Ser Val Leu Gly Asn Ala
65                  70                  75                  80

Leu Asn Lys Gly Met Ala Pro Gln Ala Asn Leu Val Phe Gln Ser Ile
                85                  90                  95

Met Asp Ser Ser Gly Gly Leu Gly Gly Leu Pro Ser Asn Leu Asn Thr
                100                 105                 110
```

```
Leu Phe Ser Gln Ala Trp Asn Ala Gly Ala Arg Ile His Thr Asn Ser
            115                 120                 125

Trp Gly Ala Pro Val Asn Gly Ala Tyr Thr Ala Asn Ser Arg Gln Val
130                 135                 140

Asp Glu Tyr Val Arg Asn Asn Asp Met Thr Val Leu Phe Ala Ala Gly
145                 150                 155                 160

Asn Glu Gly Pro Asn Ser Gly Thr Ile Ser Ala Pro Gly Thr Ala Lys
                165                 170                 175

Asn Ala Ile Thr Val Gly Ala Thr Glu Asn Tyr Arg Pro Ser Phe Gly
            180                 185                 190

Ser Leu Ala Asp Asn Pro Asn His Ile Ala Gln Phe Ser Ser Arg Gly
        195                 200                 205

Ala Thr Arg Asp Gly Arg Ile Lys Pro Asp Val Thr Ala Pro Gly Thr
    210                 215                 220

Phe Ile Leu Ser Ala Arg Ser Ser Leu Ala Pro Asp Ser Ser Phe Trp
225                 230                 235                 240

Ala Asn Tyr Asn Ser Lys Tyr Ala Tyr Met Gly Gly Thr Ser Met Ala
                245                 250                 255

Thr Pro Ile Val Ala Gly Asn Val Ala Gln Leu Arg Glu His Phe Ile
            260                 265                 270

Lys Asn Arg Gly Ile Thr Pro Lys Pro Ser Leu Ile Lys Ala Ala Leu
        275                 280                 285

Ile Ala Gly Ala Thr Asp Val Gly Leu Gly Tyr Pro Ser Gly Asp Gln
    290                 295                 300

Gly Trp Gly Arg Val Thr Leu Asp Lys Ser Leu Asn Val Ala Tyr Val
305                 310                 315                 320

Asn Glu Ala Thr Ala Leu Ala Thr Gly Gln Lys Ala Thr Tyr Ser Phe
                325                 330                 335

Gln Ala Gln Ala Gly Lys Pro Leu Lys Ile Ser Leu Val Trp Thr Asp
            340                 345                 350

Ala Pro Gly Ser Thr Thr Ala Ser Tyr Thr Leu Val Asn Asp Leu Asp
        355                 360                 365

Leu Val Ile Thr Ala Pro Asn Gly Gln Lys Tyr Val Gly Asn Asp Phe
    370                 375                 380

Ser Tyr Pro Tyr Asp Asn Asn Trp Asp Gly Arg Asn Asn Val Glu Asn
385                 390                 395                 400

Val Phe Ile Asn Ala Pro Gln Ser Gly Thr Tyr Thr Ile Glu Val Gln
                405                 410                 415

Ala Tyr Asn Val Pro Ser Gly Pro Gln Arg Phe Ser Leu Ala Ile Val
            420                 425                 430

His

<210> SEQ ID NO 4
<211> LENGTH: 275
<212> TYPE: PRT
<213> ORGANISM: Bacillus amyloliquefaciens

<400> SEQUENCE: 4

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
                20                  25                  30

Ser Gly Ile Asp Ser Ser His Pro Asp Leu Lys Val Ala Gly Gly Ala
            35                  40                  45
```

```
Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275

<210> SEQ ID NO 5
<211> LENGTH: 7
<212> TYPE: PRT
<213> ORGANISM: Artificial Sequence
<220> FEATURE:
<223> OTHER INFORMATION: Synthetic

<400> SEQUENCE: 5

Leu Asn Asn Ser Ile Gly Val
1               5

<210> SEQ ID NO 6
<211> LENGTH: 3
<212> TYPE: PRT
<213> ORGANISM: Artificial sequence
<220> FEATURE:
<223> OTHER INFORMATION: Synthetic

<400> SEQUENCE: 6

Ser Ser Asn
1

<210> SEQ ID NO 7
<211> LENGTH: 311
<212> TYPE: PRT
<213> ORGANISM: Bacillus species TY145

<400> SEQUENCE: 7

Ala Val Pro Ser Thr Gln Thr Pro Trp Gly Ile Lys Ser Ile Tyr Asn
```

```
                 1               5                   10                  15
Asp Gln Ser Ile Thr Lys Thr Thr Gly Gly Ser Gly Ile Lys Val Ala
                20                  25                  30

Val Leu Asp Thr Gly Val Tyr Thr Ser His Leu Asp Leu Ala Gly Ser
            35                  40                  45

Ala Glu Gln Cys Lys Asp Phe Thr Gln Ser Asn Pro Leu Val Asp Gly
 50                  55                  60

Ser Cys Thr Asp Arg Gln Gly His Gly Thr His Val Ala Gly Thr Val
 65                  70                  75                  80

Leu Ala His Gly Gly Ser Asn Gly Gln Gly Val Tyr Gly Val Ala Pro
                85                  90                  95

Gln Ala Lys Leu Trp Ala Tyr Lys Val Leu Gly Asp Asn Gly Ser Gly
            100                 105                 110

Tyr Ser Asp Asp Ile Ala Ala Ile Arg His Val Ala Asp Glu Ala
            115                 120                 125

Ser Arg Thr Gly Ser Lys Val Val Ile Asn Met Ser Leu Gly Ser Ser
            130                 135                 140

Ala Lys Asp Ser Leu Ile Ala Ser Ala Val Asp Tyr Ala Tyr Gly Lys
145                 150                 155                 160

Gly Val Leu Ile Val Ala Ala Ala Gly Asn Ser Gly Ser Gly Ser Asn
                165                 170                 175

Thr Ile Gly Phe Pro Gly Gly Leu Val Asn Ala Val Ala Ala
                180                 185                 190

Leu Glu Asn Val Gln Gln Asn Gly Thr Tyr Arg Val Ala Asp Phe Ser
            195                 200                 205

Ser Arg Gly Asn Pro Ala Thr Ala Gly Asp Tyr Ile Ile Gln Glu Arg
            210                 215                 220

Asp Ile Glu Val Ser Ala Pro Gly Ala Ser Val Glu Ser Thr Trp Tyr
225                 230                 235                 240

Thr Gly Gly Tyr Asn Thr Ile Ser Gly Thr Ser Met Ala Thr Pro His
                245                 250                 255

Val Ala Gly Leu Ala Ala Lys Ile Trp Ser Ala Asn Thr Ser Leu Ser
                260                 265                 270

His Ser Gln Leu Arg Thr Glu Leu Gln Asn Arg Ala Lys Val Tyr Asp
            275                 280                 285

Ile Lys Gly Gly Ile Gly Ala Gly Thr Gly Asp Asp Tyr Ala Ser Gly
            290                 295                 300

Phe Gly Tyr Pro Arg Val Lys
305                 310

<210> SEQ ID NO 8
<211> LENGTH: 269
<212> TYPE: PRT
<213> ORGANISM: Bacillus Savinase

<400> SEQUENCE: 8

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
 50                  55                  60

His Val Ala Gly Thr Ile Ala Ala Leu Asn Asn Ser Ile Gly Val Leu
```

-continued

```
 65                  70                  75                  80
Gly Val Ala Pro Ser Ala Glu Leu Tyr Ala Val Lys Val Leu Gly Ala
            85                  90                  95
Ser Gly Ser Gly Ser Val Ser Ser Ile Ala Gln Gly Leu Glu Trp Ala
           100                 105                 110
Gly Asn Asn Gly Met His Val Ala Asn Leu Ser Leu Gly Ser Pro Ser
        115                 120                 125
Pro Ser Ala Thr Leu Glu Gln Ala Val Asn Ser Ala Thr Ser Arg Gly
        130                 135                 140
Val Leu Val Val Ala Ala Ser Gly Asn Ser Gly Ala Gly Ser Ile Ser
145                 150                 155                 160
Tyr Pro Ala Arg Tyr Ala Asn Ala Met Ala Val Gly Ala Thr Asp Gln
            165                 170                 175
Asn Asn Asn Arg Ala Ser Phe Ser Gln Tyr Gly Ala Gly Leu Asp Ile
            180                 185                 190
Val Ala Pro Gly Val Asn Val Gln Ser Thr Tyr Pro Gly Ser Thr Tyr
            195                 200                 205
Ala Ser Leu Asn Gly Thr Ser Met Ala Thr Pro His Val Ala Gly Ala
        210                 215                 220
Ala Ala Leu Val Lys Gln Lys Asn Pro Ser Trp Ser Asn Val Gln Ile
225                 230                 235                 240
Arg Asn His Leu Lys Asn Thr Ala Thr Ser Leu Gly Ser Thr Asn Leu
            245                 250                 255
Tyr Gly Ser Gly Leu Val Asn Ala Glu Ala Ala Thr Arg
            260                 265
```